US009492355B2

(12) United States Patent
Ratnakar

(10) Patent No.: US 9,492,355 B2
(45) Date of Patent: Nov. 15, 2016

(54) SMART MEDICINE CONTAINER

(71) Applicant: Nitesh Ratnakar, Wheeling, WV (US)

(72) Inventor: Nitesh Ratnakar, Wheeling, WV (US)

(*) Notice: Subject to any disclaimer, the term of this patent is extended or adjusted under 35 U.S.C. 154(b) by 0 days.

(21) Appl. No.: 14/338,337

(22) Filed: Jul. 22, 2014

(65) Prior Publication Data
US 2014/0326744 A1 Nov. 6, 2014

Related U.S. Application Data

(63) Continuation of application No. 12/613,520, filed on Nov. 5, 2009, now abandoned.

(51) Int. Cl.
| | |
|---|---|
| *A61J 7/04* | (2006.01) |
| *A61J 7/00* | (2006.01) |
| *A61J 7/02* | (2006.01) |
| *G06F 19/00* | (2011.01) |
| *G07F 9/02* | (2006.01) |
| *G07F 11/44* | (2006.01) |
| *G07F 17/00* | (2006.01) |

(52) U.S. Cl.
CPC .............. *A61J 7/0084* (2013.01); *A61J 7/02* (2013.01); *A61J 7/0481* (2013.01); *G06F 19/3462* (2013.01); *G07F 9/02* (2013.01); *G07F 11/44* (2013.01); *G07F 17/0092* (2013.01); *A61J 7/049* (2015.05); *A61J 7/0418* (2015.05); *A61J 7/0436* (2015.05)

(58) Field of Classification Search
CPC .. G07F 17/0092; A61J 7/0445; A61J 7/0481
See application file for complete search history.

(56) References Cited

U.S. PATENT DOCUMENTS

| | | | | | |
|---|---|---|---|---|---|
| 5,472,113 | A | * | 12/1995 | Shaw | A61J 7/0084 221/15 |
| 6,131,399 | A | * | 10/2000 | Hall | G06Q 10/087 705/28 |
| 6,304,797 | B1 | * | 10/2001 | Shusterman | A61B 5/02055 700/236 |
| 8,357,114 | B2 | * | 1/2013 | Poutiatine | A61J 7/0038 604/59 |
| 9,016,516 | B2 | * | 4/2015 | Ortenzi | A61J 7/0076 221/2 |
| 2003/0222090 | A1 | * | 12/2003 | Abdulhay | G07F 11/10 221/3 |
| 2005/0150488 | A1 | * | 7/2005 | Dave | A61J 7/0481 128/200.14 |

* cited by examiner

*Primary Examiner* — Timothy Waggoner
(74) *Attorney, Agent, or Firm* — Jundong Ma

(57) ABSTRACT

A smart medicine container is provided to secure accesses to a bulk supply of pills stored therein and pills dispensed therein. The medicine container comprises a control unit, a memory, a communication interface unit, a pill-supply housing configured to store a bulk supply of pills, a pill-supply locking means configured to lock access to the pill-supply housing, a dispensing assembly configured to dispense pills from among the bulk supply of pills, and a dispensed-pill housing configured to receive and store dispensed pills, a dispensed-pill locking means configured to lock access to the dispensed-pill housing. The control unit is programmed to irreversibly cause the pill-supply locking means to lock access to the pill-supply housing and irreversibly cause the dispensed-pill locking means to lock access to the dispensed-pill housing when receiving information indicating that the bulk supply of pills should permanently discontinue to be taken by a patient.

14 Claims, 18 Drawing Sheets

SMART MEDICINE CONTAINER

CROSS-REFERENCE TO RELATED APPLICATION

This application is a continuation application claiming priority under 35 U.S.C. §120 to U.S. Non-provisional patent application Ser. No. 12/613,520, filed on Nov. 5, 2009, which is a continuation-in-part application claiming priority under 35 U.S.C. §120 to each and all of the following U.S. patent applications:
  a) U.S. Non-provisional patent application Ser. No. 10/905,032, filed on Dec. 11, 2004, now U.S. Pat. No. 7,269,476;
  b) U.S. Non-provisional patent application Ser. No. 11/775,611, filed on Jul. 10, 2007, now abandoned, which is a divisional application claiming priority under 35 U.S.C. §121 to the aforesaid U.S. Non-provisional patent application Ser. No. 10/905,032;
  c) U.S. Non-provisional patent application Ser. No. 12/267,555, filed on Nov. 7, 2008 which is a continuation-in-part application claiming priority under 35 U.S.C. §120 to the aforesaid U.S. Non-provisional patent application Ser. No. 10/905,032;
  d) U.S. Non-provisional patent application Ser. No. 12/488,879, filed on Jun. 22, 2009, which is a continuation-in-part application claiming priority under 35 U.S.C. §120 to each and both of the aforesaid U.S. Non-provisional patent application Ser. Nos. 10/905,032 and 12/267,555; and
  e) U.S. Non-provisional patent application Ser. No. 12/611,912, filed on Nov. 3, 2009, now U.S. Pat. No. 8,483,872, which is a continuation-in-part application claiming priority under 35 U.S.C. §120 to each and all of the aforesaid U.S. Non-provisional patent application Ser. Nos. 10/905,032, 11/775,611, 12/267,555 and 12/488,879.

All of the aforesaid prior patent applications are incorporated herein by reference in their entirety.

FIELD OF INVENTION

The present invention relates to medicine containers, more specifically to a medicine container having storage, counting and dispensing compartments and having an inbuilt pill dispensing apparatus having means to automatically dispenses a prescribed quantity of medicine at prescribed times. According to another aspect, a pill recovery system and apparatus is disposed inside the medicine container having means to recover pills remaining in the counting compartment of the medicine container after completion of a dispensing cycle; and deposit recovered pills back into the storage compartment of the medicine container to be used in future dispensation cycles.

BACKGROUND AND PRIOR ART

The advances in medicine are enhancing the quality and longevity of human lives. Ailments, for which there were no effective treatments before, are now effectively treated by one or more drugs. In many cases, patients have to remember to take a dose of medicine at prescribed times. A number of ailments require treatment with one or more combination of medicines. With most medicines (e.g., pills, syrups), doses have to be taken at specific intervals (every six hours) or at certain times of the day (morning, afternoon, evening, before bed time etc). A patient may have difficulty remembering to take medicine at recommended times. Sometimes, patients have difficulty remembering that they have already taken a dose. Some patients have difficulty remembering the recommended dose of medicine to be taken, especially if a medicine dose requires more than one pill of the same medicine. In a multiple drug regimen, such a scenario is even more convoluted and may pose grave consequences to the patient. This is especially true for patients with inadequate skills or knowledge to follow a medicine regimen like elderly, disabled and cognitively impaired and patients with psychiatric disorders (Levy R L et al, American Journal of Gastroenterology 1999; 94:1733-1742 & Nigro J, Journal of Clinical Gastroenterology 2001; 32:66-82). This segment of the population is the most vulnerable as their medicine regimen usually comprises of multiple medicines, each with a different schedule and a different set of instructions. In addition, eyesight fade with age and reading labels of medicine containers can present a problem. Even young and alert patients are sometimes overwhelmed by life, work, family and other responsibilities and forget to take their medicines. This is especially apparent with temporary treatments, such as antibiotics, where the medicine is only taken for a short period of time. In this case, patients are unable to generate a routine based around taking the medicine. The end result of the above situations is that the amount of medicine taken is either too low to affect the course of the ailment, or is too high and causes overdose reactions.

There are many studies that show that management of chronic diseases is unsatisfactory in spite of the great advances in medicine. Factors that have been implicated are 1) poor compliance with medicine regimen because patients forget to take their medicines 2) frequent need to go the pharmacist for refills and education 3) need for frequent visit to the health care professional's office to monitor the treatment response and to make any required changes in medicine regimen 4) lack of adequate health education and inadequate reinforcement thereof 5) under or over dosing of medicine 6) altered dosing regimen 7) incorrect administration of medicine (Kane S et al, Advanced Therapy for Inflammatory Bowel Disease; 2002: 9-11). Even more worrisome is the practice that patients do not inform physicians of their non compliance with medicine regimen. Physicians, in such a case, conclude that patient's condition is not responding to the current medicine regimen and make changes in medicine dose, add or substitute another medicine. This results in unnecessary changes in patient's medicine regimen which can be detrimental to the health of the patient. This practice also increases health care cost.

Medicines including pills, capsules, tablets, caplets and the like have traditionally been packaged in bottles or other such containers capped with a variety of closure devices. The caps or closures for these containers have taken a variety of forms and, more recently, have included a key system, depress-and-turn system, or the like, designed to prevent small children from gaining access to the contents. These medicine containers do not have features to assist patients remember to take their medicines or to record their compliance with a medicine regimen. There are many prior art attempts to address problems of this nature which generally incorporate some type of a time, date or dosage indicating device on the cap or other part of the container which involves a movable pointer or other such device designed to be indicative of the status of medicine administration. These devices generally involve the relative motion of a pointer, plate or other indicator relative to a dial which is moved each time the medicine container is used to indicate the fact that the medicine has been taken and/or the time when the next dose is due.

Systems including a pointer and dial indicator on the container cap are illustrated. In U.S. Pat. No. 5,279,422, Adams disclosed a device suitable as a closure cap for a medicine container. The device has indicia circumferentially marked on the upper surface of the device representing the time for next taking the medicine in the container. An arm rotatably and pivotably mounted in the center of the device is set to point at the time for next taking the medicine. The arm is releasably retained in position by cooperating pegs and indentations on the upper surface of the device and the underside of the rotatable arm. In U.S. Pat. No. 5,216,975, Bartholomew disclosed a combination medicine container cap and indicator device adapted to function as the closure or cover for a medicine container or container. The device includes an indicator providing a visual indication for the user that a pill has been or should be removed from the bottle for consumption. While these approaches are viable as long as they are properly used, the indicating position is easily altered and presents no reliable permanent record.

Various other devices include mechanical advancing systems that coordinate with the operation of the bottle cap. In U.S. Pat. No. 4,753,189, Mastman et al, disclosed a medicine bottle unit having a closure for indicating dosage and other information, which changes automatically as the closure is rotated on the bottle of the unit. The closure includes an outer cap and an inner member within the cap. The cap and inner member have co-operable indicia thereon. The inner member moves with the cap as the cap is rotated in one direction on the bottle. However, the cap moves relative to the bottle and the inner member when the cap is rotated in the opposite direction on the bottle, thus assuring a change in the information represented by the indicia on the cap and the indicator on the inner member, or by indicia on the inner member visible through a hole in the cap. Several embodiments of medicine bottle unit are disclosed. In U.S. Pat. No. 5,975,010, Marshall disclosed indicators and methods of indicating which are intended primarily for use with medicine containers. The devices typically indicate the number of doses of medicine ingested or remaining to be taken by a patient during a particular period. These devices additionally provide tactile assistance to patients in appropriately repositioning the indicator arms and, when used correctly, may reduce the possibility of patient overdose by restricting improper attempts to advance the indicator arm. In U.S. Pat. No. 4,405,045, Villa-Real disclosed a color-coded, two-component medicament container comprising a cap means with variously pre-set structural interval spacing between each pair of preformed window system to differentiate a fixed three-hour time interval cap from a four-hour interval cap, a six-hour time interval cap, an 8-hour time interval cap and from a unitary pre-formed window for a 12 or 24-hour time interval cap; each kind of cap to be specifically used according to the prescribed frequency of drug administration such as every 3-hour frequency, every 4-hour frequency, every 6-hour frequency, every 8-hour frequency and every 12 or 24-hour frequency, respectively, as coordinated in a snug-fitting but csafety lock wisely rotatable engagement with a complementarily shaped cylindrical medicament container having csafety lock-like numeral indicia ranging from 1 to 12 and equidistantly arranged as in a csafety lock there around the supper circumferential exterior wall of the said medicament container is disclosed.

Both, use of the dial or pointer devices and operation of container cap, require manual dexterity and intact cognition. Moreover, with these devices, patients have to learn complex instruction each time a change is made in medicine dose or frequency. Both these are problematic in elderly, disabled or in patients with cognitive impairment.

The need for a device that automatically dispenses the proper pill(s) in the proper amount(s) at the proper time(s) each day and alerts the user to take the dispensed pill(s) is evident by the numerous devices described in the prior art. In U.S. Pat. No. 4,915,256, Tump disclosed a dispensing assembly for dispensing a series of different pills over a prescribed period. The dispensing assembly is provided with an indicator that is adjustable to preset the start of the pill regiment on whatever day desired. The pill package and dispensing assembly are constructed and arranged so that after the indicator has been preset, the pill package can be fixedly positioned in the dispensing assembly with the first pill of the regimen in position to be taken by the user on the first pre selected day. In U.S. Pat. No. 5,915,589, Lim has disclosed a device that can be loaded with appropriate pills and programmed to automatically dispense the proper amount(s) and proper type(s) of pill(s) at the proper time(s) each day. The device also includes a system for alerting the pill taker that pills have been dispensed and need to be taken, a system for providing voice messages to coach the pill taker to use the device and consume the pills, a system for alerting an off-site caregiver when the pill taker has not responded as required or when there is a problem with the operation of the device, and a system for an efficient and accurate loading of pills into the device.

In U.S. Pat. No. 4,573,606 Lewis et al., in U.S. Pat. No. 4,674,651 Scidmore et al., in U.S. Pat. No. 4,838,453 Luckstead and in U.S. Pat. No. 5,044,516 Hoar have described an automatic pill dispensing assembly that has pill storage regulating wheels that are rotated constantly by electric safety lock motors. The constantly rotating pill storage regulating wheel of these devices successively moves each pill storage compartment of the regulating wheel into a temporary alignment with a pill discharge outlet at a cyclical and fixed time interval. When a pill storage compartment is in alignment with the pill discharge outlet, any pill stored in the compartment will fall by gravity through, the outlet into a pill receptacle. Automatic pill dispensing assemblies that do not employ rotating wheels are also known. For example, U.S. Pat. No. 4,763,810 to Christiansen shows a device that uses a series of pill storage compartments that are arrayed in a checkerboard fashion and U.S. Pat. No. 4,798,309 to Stone et al shows a device that uses a series of pill storage compartments that are spirally arranged on an elongate cylinder. Although these examples seem to be different, the basic operating principle of all these dispensing assemblies, are nonetheless similar.

However, there are problems with the devices described in the prior art. These devices entail loading of individual pill storage compartments by the pharmacist. This is a time consuming and manpower intensive process that makes these devices costly and inefficient. None of these devices provide the ease and cost effectiveness of the present day throwaway plastic medicine containers where a bulk supply of medicaments can be dispensed at one time.

There have been many prior art attempts to incorporate a device into the medicine container that is able to record the opening and closures of the caps of the medicine containers. These prior arts have attempted to use the operation of the closure of medicine container as a surrogate marker for compliance. In U.S. Pat. No. 6,604,650 Sagar has proposed a medicine-dispensing system that has a medicine reminder to assist the patient in following a drug regimen. In an example embodiment, a medicine reminder comprises a timer programmable to a predetermined interval. A user-alert is responsive to the timer, reminding the user to take a dose of medicine at the predetermined interval. A sensor detects whether the medicine container cap has been opened and a dose-indication informs the user of the time since the last dose. The dose indication further informs the user as to whether to take a next medicine dose. The time of the last dose is determined by the timer receiving a signal from the sensor. A communications interface enables programming of a parameter associated with administering a medicine.

There are major disadvantages to the inventions that rely on medicine container cap removal as a measure of compliance. Medicine containers with cap allow access to the bulk medicine supply during each dispensing event. Once the device recognizes the removal of the cap, any number of doses may be removed from the bottle without proper recognition, thus seriously compromising the device's ability to properly record compliance. Even more troublesome is the possibility that the cap device might not be reinstalled on the bottle; if not, the subsequent removal of medicines from the bottle go unmonitored.

In addition, the devices described in prior inventions share some common drawbacks that include: 1) none of the prior art devices have the ability to automatically count and dispense a prescribed quantity of medicine at prescribed times from a bulk supply within the medicine container. 2) These devices do not provide any protection against abuse of prescription medicines. Once the closure is opened any number of doses can be removed. This is of particular concern with medicines that have a high abuse potential such as morphine. 3) The prior art devices do not provide any protection against the consumption of medicines that have expired. Medicines that are beyond their expiry date are associated with significant life threatening side effects. 4) They do not provide security features to prevent use by a person other than the intended patient. 5) Devices proposed by the prior inventions do not allow for remote medicine management. Whenever a change is made to a medicine regimen, a new prescription has to be filled and the medicine container has to be taken to the pharmacist for a change of label. The patient has to learn new information regarding the new dosage regimen. These are major deterrents to continued compliance with pharmacotherapy for chronic medical conditions. 6) Prior art devices do not assist with comprehensive disease management. Adequate disease management requires frequent monitoring of health related parameters to assess the efficacy of medicines. Studies have shown that frequent home based monitoring of health parameters and subsequent prompt adjustment of treatment regimens significantly improves disease outcomes. At the present time, such monitoring, reporting and adjustment of medicine regimen requires intensive participation by patients, including multiple visits to health care professional's office. Prior art devices do not provide a solution to this problem. 7) The devices of prior inventions are cumbersome and expensive to manufacture. None of the prior inventions have provided the necessary reliability and inexpensive implementation to present itself as a viable, alternative to today's plastic throwaway medicine containers. The value of additional features suggested by the prior inventions, have not justified the added costs.

Some prior art devices provide limited solution to individual problems faced by patients, health care professionals and pharmacists in ensuring compliance. However none of these devices have provided a comprehensive one stop solution to manage the multiple complex problems that hinder patient's compliance with a medicine regimen. Hence, while "childproof" construction has been mandated, to date there has been no other major addition to the conventional throw away plastic medicine containers.

SUMMARY OF INVENTION

Present invention discloses a dispenser (smart medicine container) having means to dispense desired number of pills from a bulk supply of pills contained in the dispenser. The dispenser comprises of first storage compartment having bulk supply of pills and having a discharge port emptying into second counting compartment. The counting compartment contains first and second conveyors moving at first and second speed; wherein the second speed is greater than the first speed thereby enabling pill separation; the second conveyor discharging pills into third dispensing compartment. Sensors are strategically placed along the conveyors to count pills discharged into dispensing compartment. A pill recovery system and apparatus is disposed inside the dispenser having means to recover pills remaining on first and second conveyors upon completion of a dispensation cycle and there after deposit recovered pills back into the storage compartment for use in future dispensation cycles.

DETAILED DESCRIPTION OF THE PRESENT INVENTION

Figure 1A:
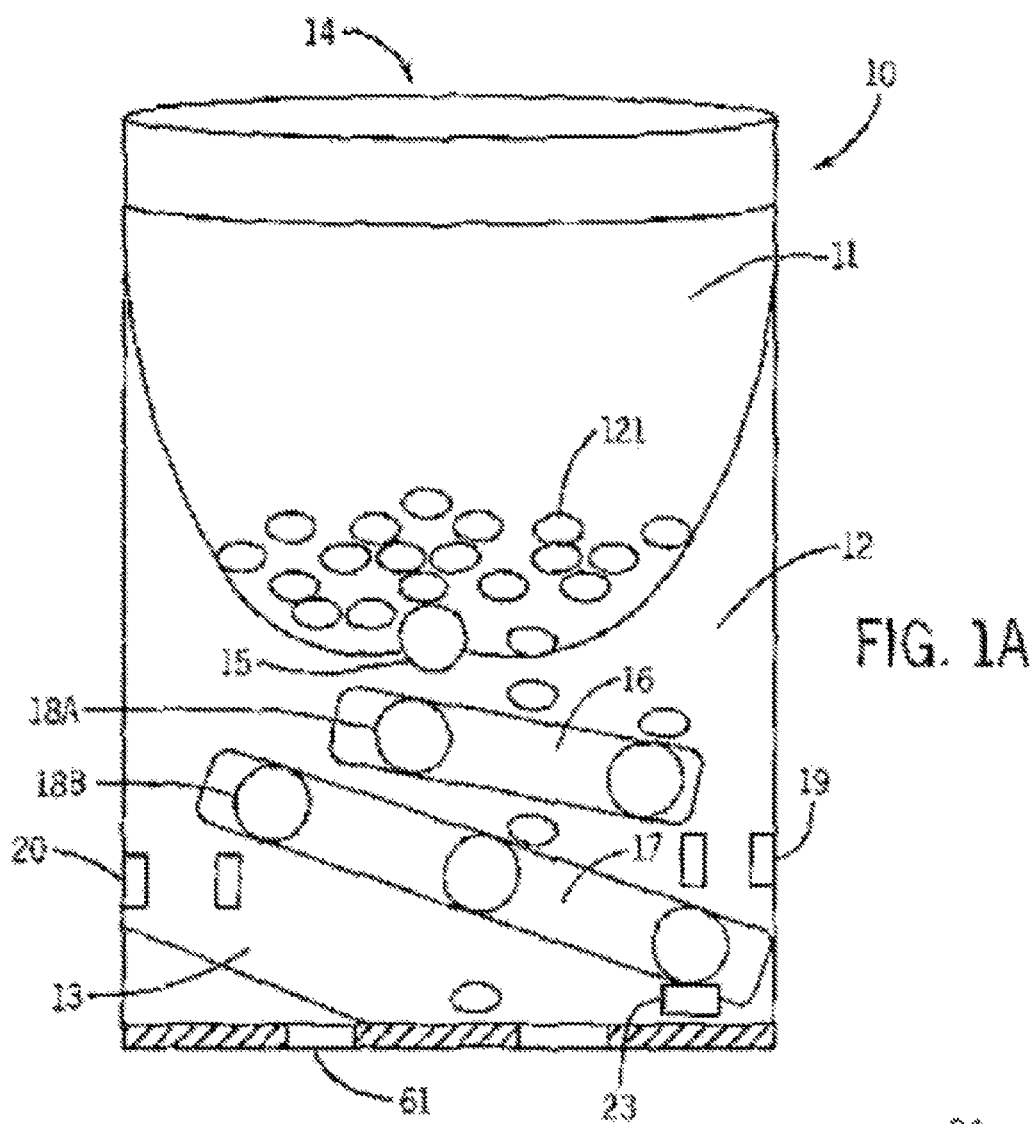
FIG. 1A is a coronal section of the smart medicine container and shows the pill dispensing assembly built into the medication container itself.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out One or several purposes of the present invention. It is important, therefore, that the claims be regarded as including such equivalent constructions insofar as they do not depart from the spirit and scope of the present invention.

Figure 1B:
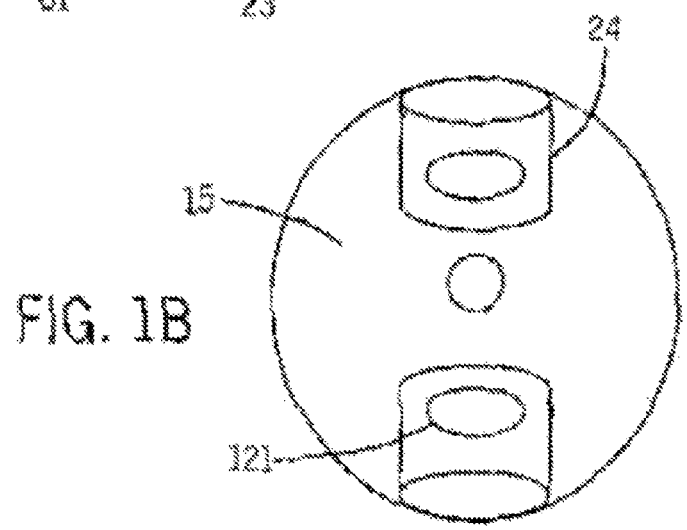
FIG. 1B shows the regulating wheel with two pill receptacles.
Figure 3:
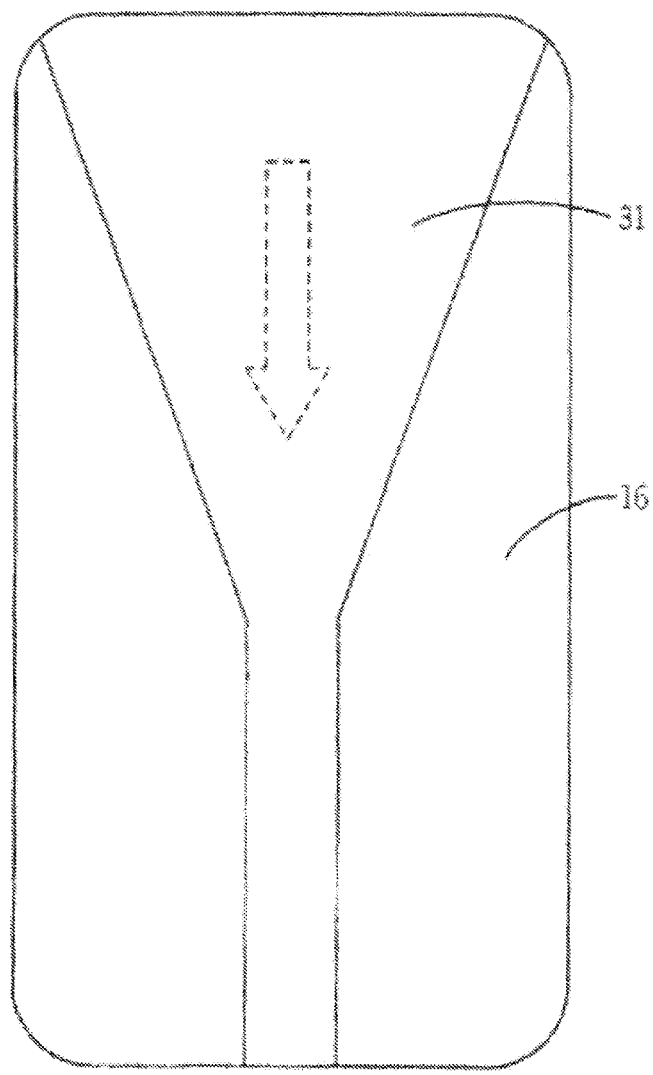
FIG. 3 shows the collecting conveyor with a 'Y' shaped pill organizer located above it.

Medicine Container:

As shown in FIG. 1A, the present invention comprises of a smart medicine container (10) that has an inbuilt pill dispensing assembly. The medicine container in the preferred embodiment is elliptical in shape but it may be of any convenient shape and size. It has three compartments—storage compartment (11), counting compartment (12) and dispensing compartment (13) that is stacked on top of one another. The storage compartment (11) is located at the top and is 'U' or 'V' shaped. It has an aperture at the bottom to allow the passage of pills (121) into the counting compartment (12) which is guarded by a regulating wheel (15). The pill dispensing assembly of the present invention has an inbuilt pill counting apparatus that provides the means to automatically dispense a desired quantity of medicine at desired times from a bulk supply within the smart medicine container (10). The pill dispensing assembly comprises of a regulating wheel (15) will two pill receptacles (24), a collecting conveyor (16), a dispensing conveyor (17), motors to power the conveyors and the regulating wheel and a multitude of photoelectric sensors placed along the path of relay of the pills (121). A printed circuit board (71) present within the smart medicine container regulates the operation of the entire pill dispensing assembly. The regulating wheel (15) is powered by a motor (not shown) and has two pill receptacles (24) placed at 180 degrees from each other (FIG. 1B). It guards the aperture between the storage and counting compartments. The pill receptacles (24) collect pills (121) when facing the storage compartment (11) and discharge them onto the collecting conveyor (16) when facing the counting compartment (12). The regulating wheel (15) provides the means for a controlled and orderly discharge of pills (121) from the storage compartment onto the collecting conveyor (16) in the counting compartment (12). The regulating wheel (15) also prevents migration of pills (121) out of the storage compartment (11) when it remains idle. The counting compartment (12) is located in the middle and has a collecting conveyor (16) on top, a dispensing conveyor (17) below and photoelectric sensors (19&20) that line the path of relay of pills (121) along the conveyors. The collecting conveyer conveyor (16) has a 'Y' shaped pill organizer (31) located above its surface, shown in FIG. 3, which aligns the pills (121) in one column for an orderly discharge onto the dispensing conveyer conveyor (17). In the preferred embodiment shown in FIG. 1A, the passageway from the collecting conveyer conveyor (16) to the dispensing conveyer conveyor (17) has photoelectric sensors (19), but any other suitable sensing instrument can be used. The dispensing conveyor (17) collects pills (121) from the collecting conveyor (16) and discharges them into the dispensing compartment (13). The dispensing conveyor (17) again has a 'Y' shaped pill organizer located above its surface which aligns the pills (121) in one column for an orderly discharge into the dispensing compartment (13). In the preferred embodiment, the passageway from the dispensing conveyer conveyor (17) to the dispensing compartment (13) has photoelectric sensors (20), but any other suitable sensing instrument may be used. The collecting and the dispensing conveyors move on two separate sets of wheels (18A&18B) that are powered by motors (not shown). In the preferred embodiment, the speed of the dispensing conveyor (17) is greater than of the collecting conveyor (16). The dispensing compartment (13) is located at the bottom and has an outlet door (22) through which pills (121) is dispensed to the patient. The outlet door (22) has a sensor (23) which captures its operation.

Figure 2:
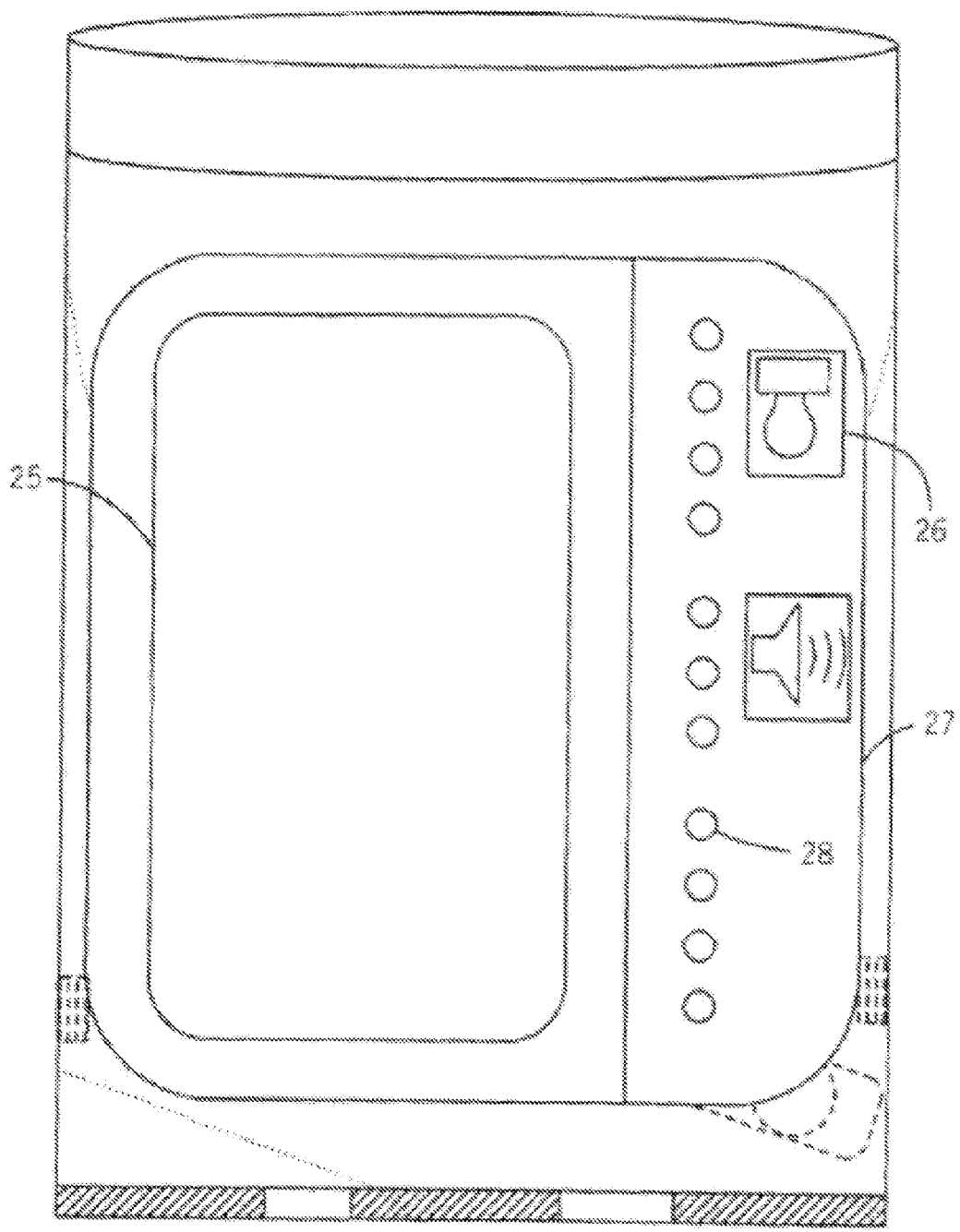
FIG. 2 is a front view of the smart medicine container showing the electronic display unit, audio speakers, visual alarm and a plurality of control switches.

FIG. 2 shows the anterior aspect of the smart medicine container. A plurality of control switches (28) are provided that can be used for multiple purposes, including but not limited to—1) as a keypad for command and data entry 2) to actuate display of compliance data and other information in different formats 3) as a keypad for operation of the universal safety lock (73). An audio speaker (27) and a visual alarm (26) are provided that inactivated when a dose of medicine is ready to be taken. FIG. 2 also shows an electronic display unit (25), which in the preferred embodiment is a liquid crystal display (LCD) screen.

Figure 4:
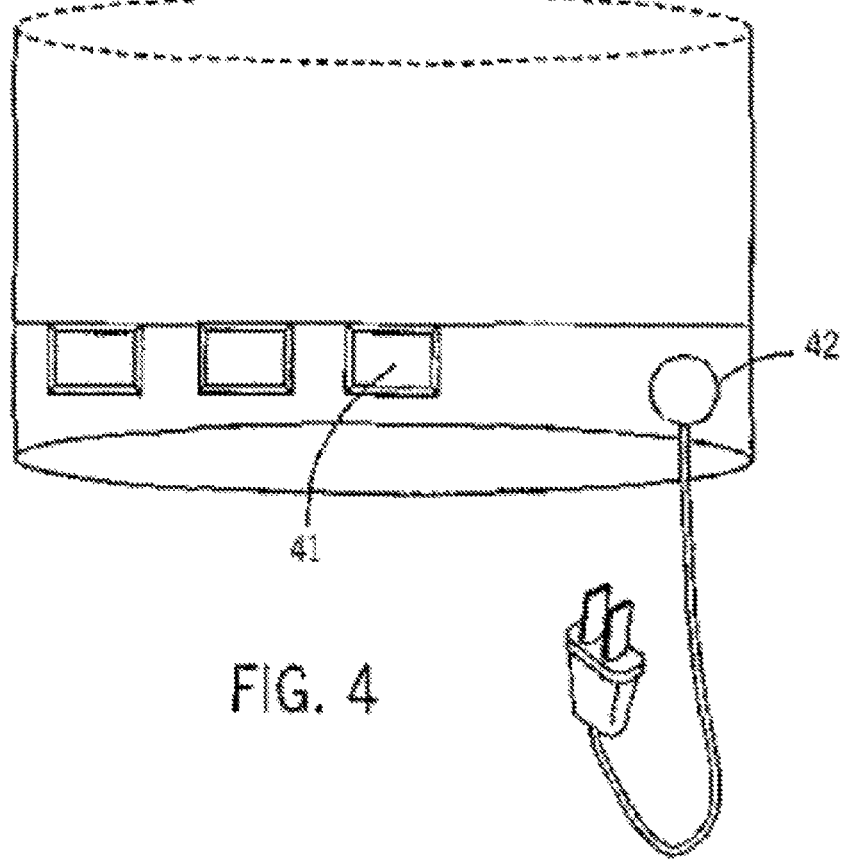
FIG. 4 is a posterior view of the lower part of the smart medicine container showing the communication ports and electrical inlet.
Figure 5:
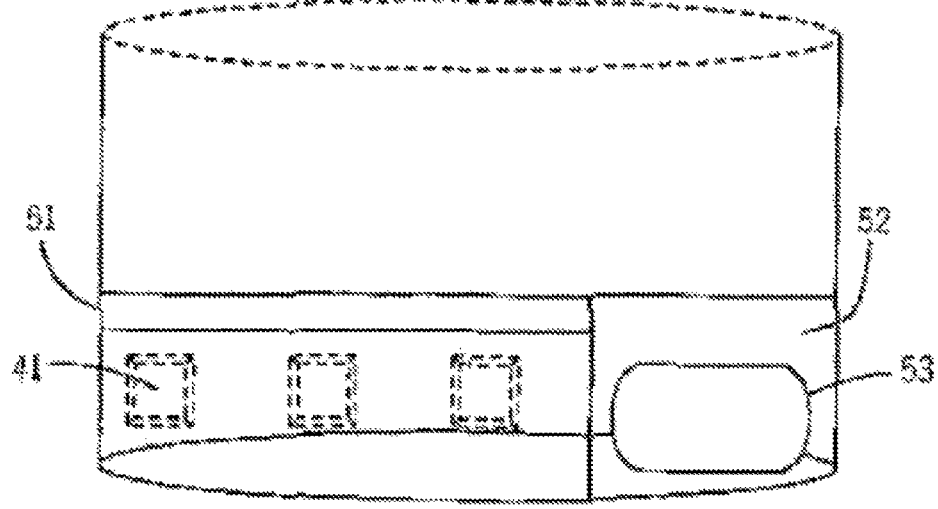
FIG. 5 is a coronal section of the lower part of the smart medicine container showing the modem with wireless transceiver, communication ports and battery compartment with a battery.

FIGS. 4 & 5 show the posterior and saggital views of the lower part of the smart medicine container respectively. A modem (51) and three communication ports (41) are provided which enable the smart medicine container (10) to send and receive communication from external devices such as web server, personal computer etc. via telephone line, wireless network, internet, LAN or any other communication network. In the preferred embodiment, the modem (51) also contains a wireless two-way transceiver. Alternatively, the wireless transceiver can be present separately. Data can be transferred between the smart medicine container (10) and a computing device such as web server, pharmacy or physician computer using the communication ports (41). A battery compartment (52) containing a battery (53) is provided which powers the smart medicine container. In addition, an electrical inlet (42) is provided which serves as an alternate source of power for the smart medicine container.

Figure 7:
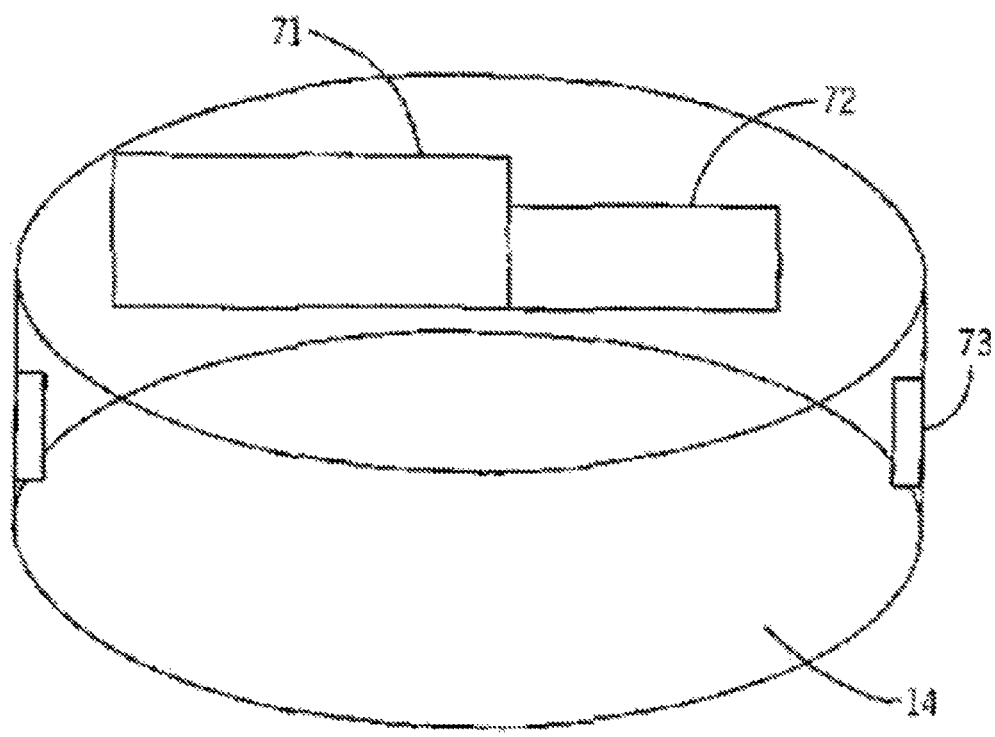
FIG. 7 is a transparent view of the cap of the smart medicine container showing the printed circuit board, memory chip and universal safety lock.

The smart medicine container (10) is covered on top by a cap (14) shown in FIG. 7. In the preferred embodiment, the cap (14) has a universal safety lock (73) that is operable by a unique combination of numbers or any other user specific identifier that is entered using the control switches (28). Alternatively, the universal safety lock (73) can be coupled with a radio frequency identification (RFID) reader. The universal safety lock (73) in this case is operable when the RFID reader reads an authorized RFID tag. Authorized users having an authorized RFID tag will be able to operate the universal safety lock (73). The safety lock (73) adds a safety feature to the smart medicine container (10) and allows only authorized access to the contents thereof. The smart medicine container (10) has an internal printed circuit board (71) and a memory chip (72) located in the cap (14). The electronic apparatus of the smart medicine container (10) is hardwired to the printed circuit board (71) and memory chip (72). The printed circuit board (71) is programmed to execute various functions of the smart medicine container (10) including, but not limited to, data analysis, operational control of electro-mechanical components, and external communication. The memory chip (72) stores operational data, information about the contained medication and any other relevant patient information. The smart medicine container (10) has an internal clock with a timer (not shown) which triggers the time sensitive functions of the smart medicine container (10). The memory chip also records instances of user taking a dispensed dose of medicine out of the smart medicine container which serves as a surrogate data for patient compliance with prescribed medication regimen.

Figure 13A:
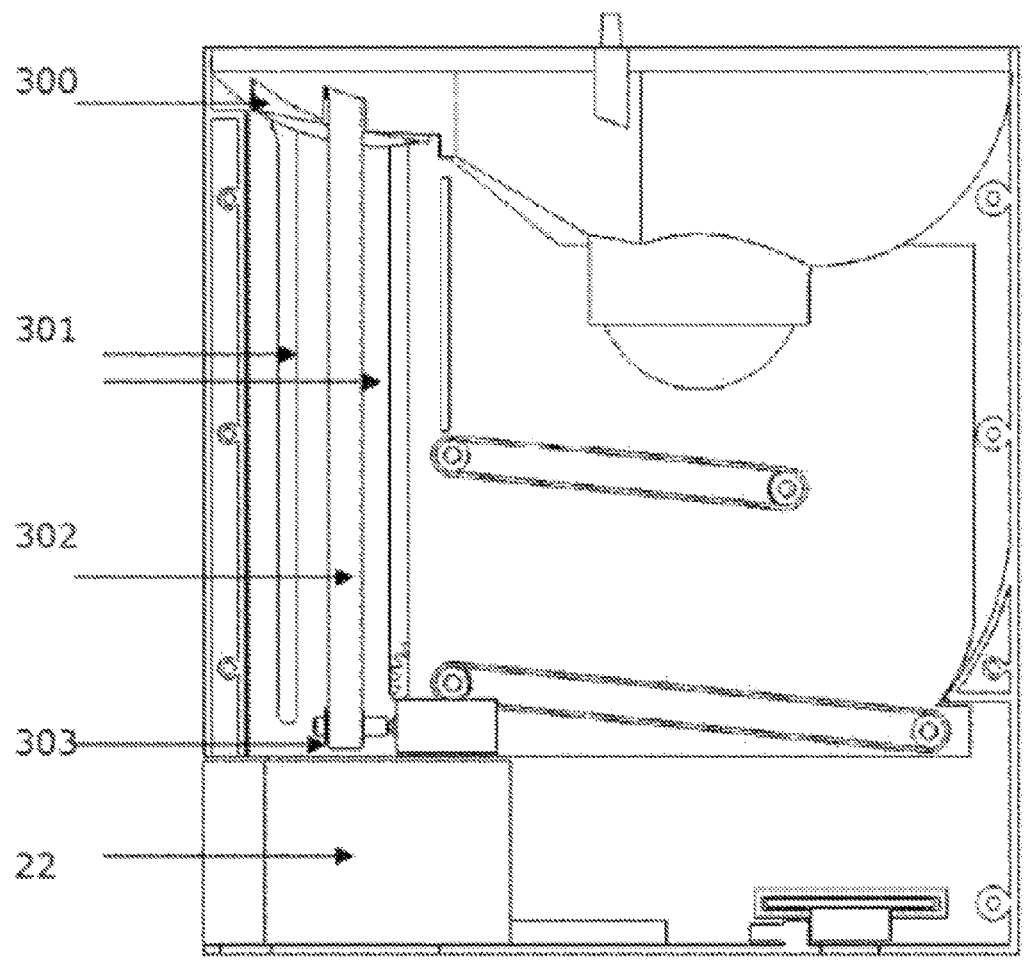
FIGS. 13A-E show the construction and operation of pill recovery apparatus and system disposed inside the smart medicine container.
Figure 13B:
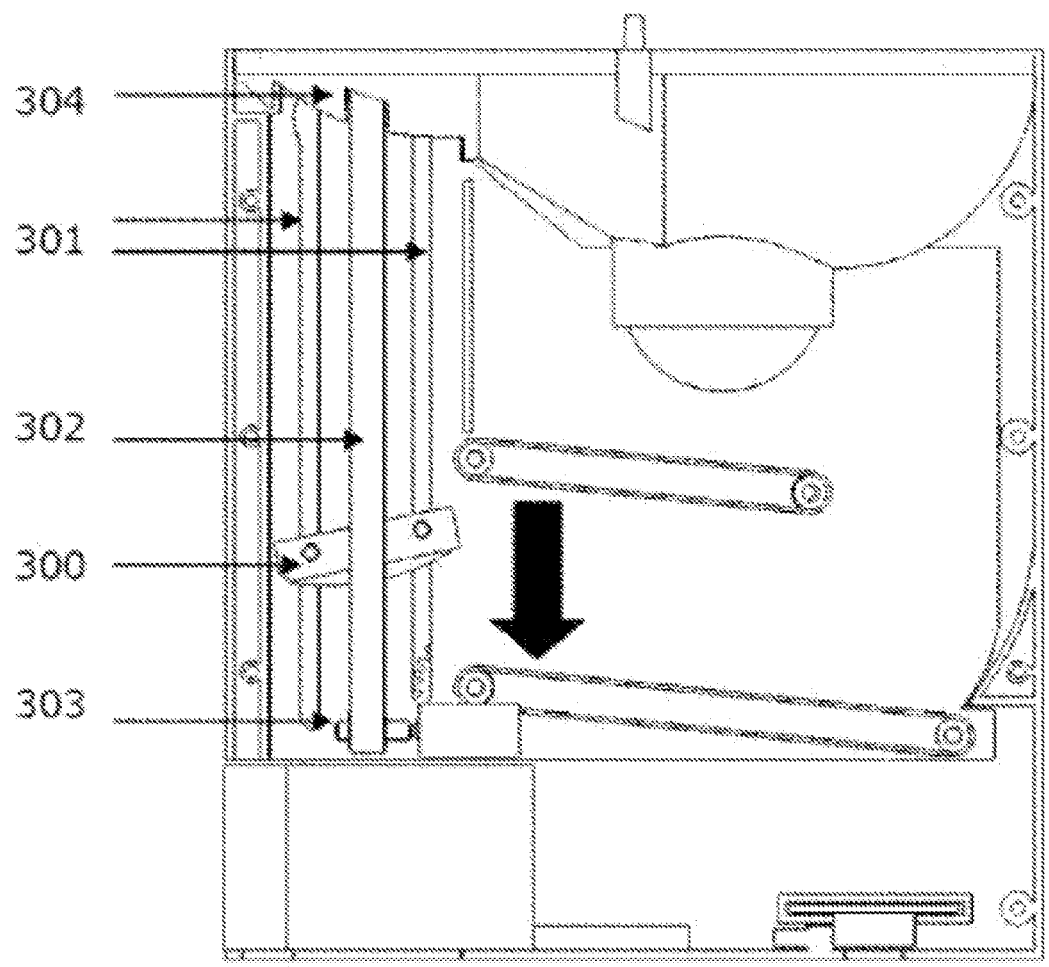
Figure 13C:
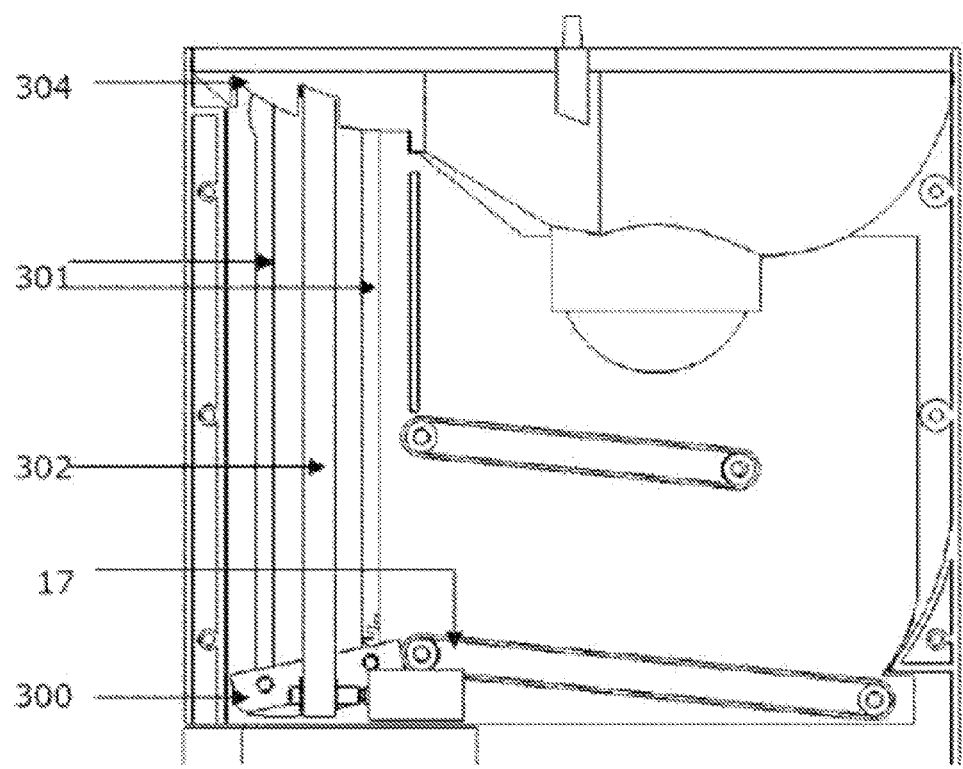
Figure 13D:
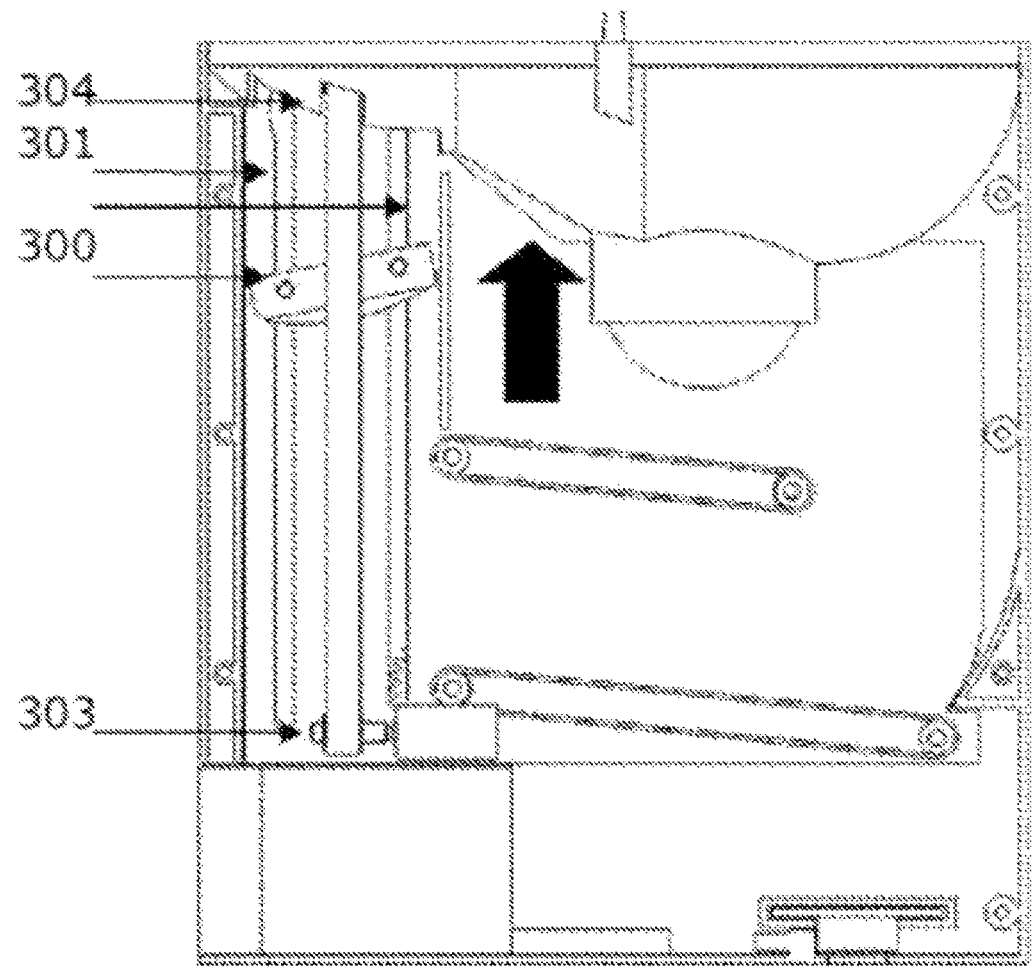
Figure 13E:
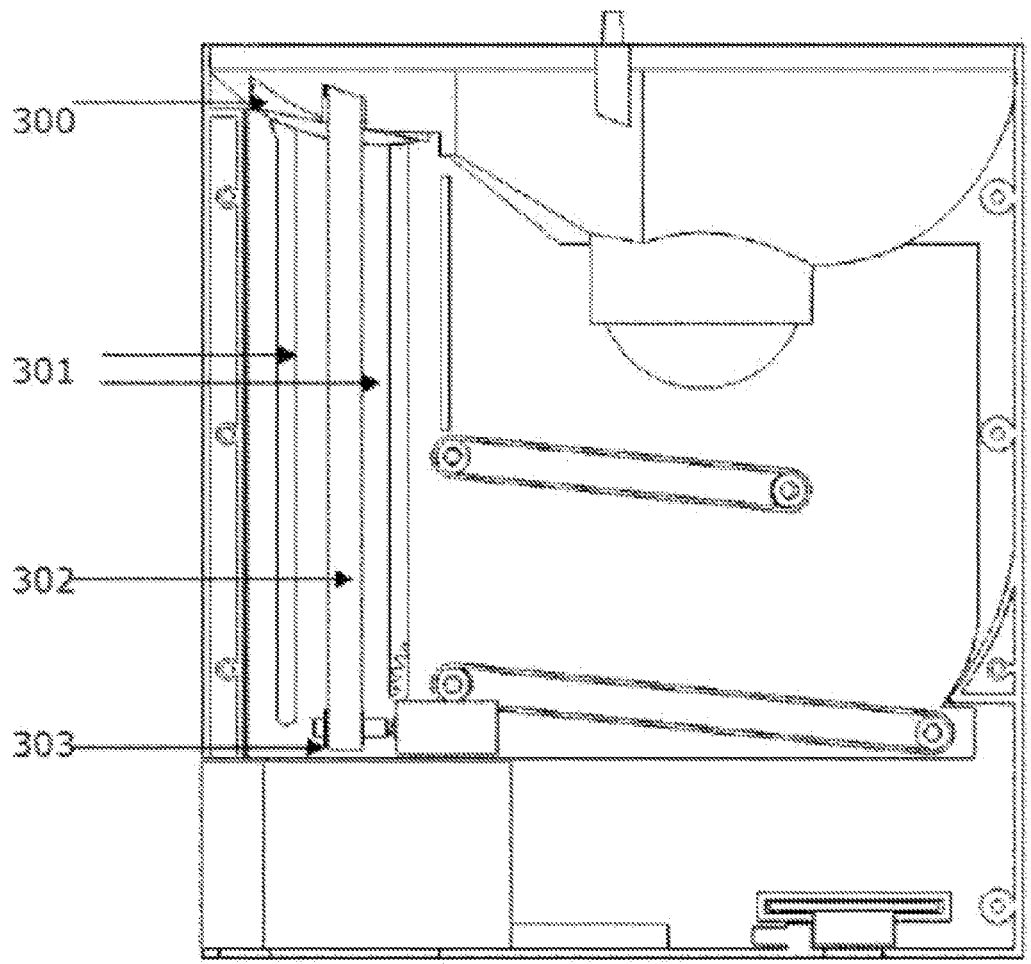

Now turning our attention to FIGS. 13A-E; a pill recovery system and apparatus is disclosed. The pill recovery system and apparatus is designed to recover pills left on the collecting and dispensing conveyors after completion of a dispensation cycle. It comprises of a recovery cup (300) disposed in resting position, as shown in FIG. 13A, flush with a corresponding defect in storage compartment (304). The recovery cup (300) is operatively connected by means of belt (302) to a recovery motor (303). The recovery motor (303) is disposed at the bottom of the smart medicine container as shown in FIGS. 13A-E. Storage compartment has a defect (304) corresponding to recovery cup (300) that accommodates the recovery cup (300) in resting position. The recovery cup (300) is reversibly movable from first resting position, as in FIG. 13A, to second recovery position, as in FIG. 13C, just below the outlet end of the dispensing conveyor (17). The recovery cup (300), while in transit between resting and recovery positions, is inclined outwards from the counting compartment such that it prevents pills contained in the recovery cup from falling into the counting compartment; as is shown in FIGS. 13B & 13D. In resting position, the recovery cup (300) is inclined such that it is inclined towards the center of gravity of the storage compartment and thereby deposits pills contained therein into the storage compartment; as is shown in FIGS. 13A & 13E. The opposite inclination of the recovery cup (300) between resting and recovery/transit positions is achieved by means of varying length of the grooves (301) that holds the recovery cup (300) in position within the smart medicine container; as shown in FIGS. 13A-E. A vertical plate separates the recovery plate from the counting compartment. Although recovery system in the preferred embodiment comprises of a recovery cup, other contraptions such as a recovery box, recovery plate etc. may as well be used with similar end result. Similarly the recovery motor may be placed at a different location while achieving the same end result. The configuration and relative placement of the components of the recovery system and apparatus should not be considered limiting.

Figure 6:
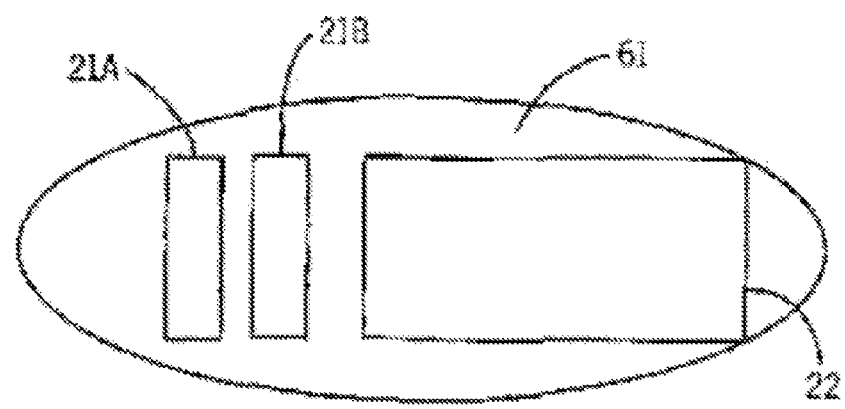
FIG. 6 is a view of the bottom surface of the smart medicine container showing the docking port, electrical port and the outlet door.
Figure 8:
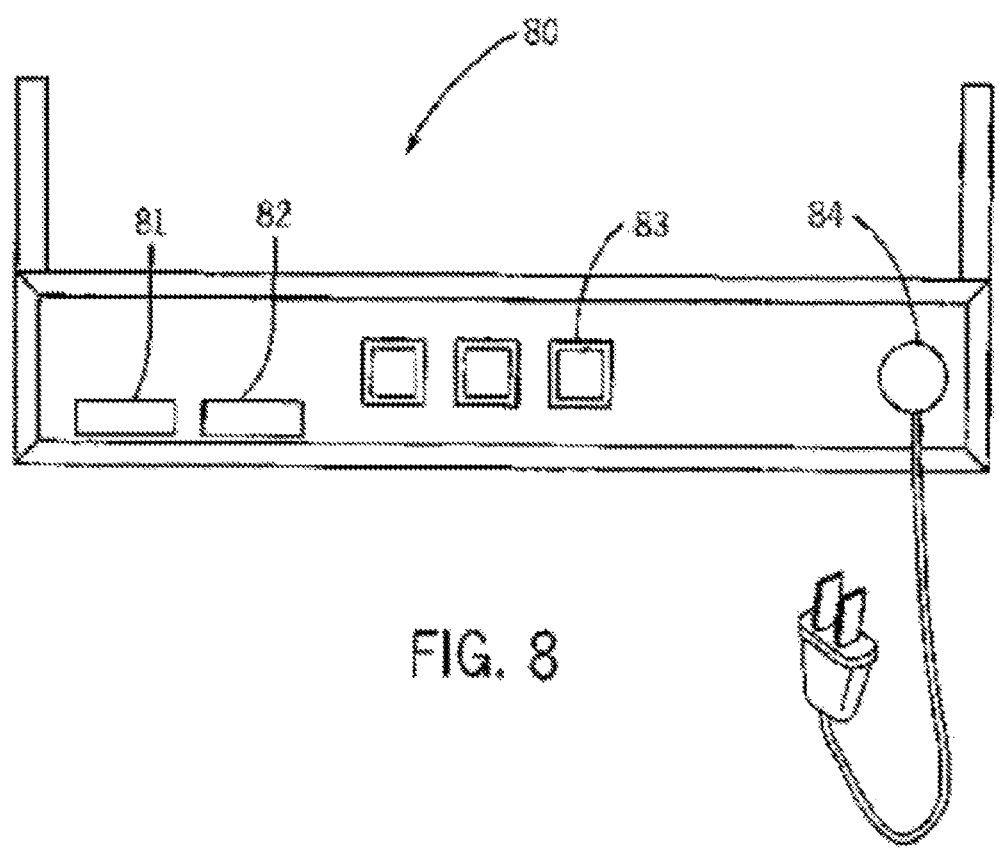
FIG. 8 is a posterior view of the sync cradle showing the docking terminal, electrical terminal, communication ports and electrical inlet.

Now referring to FIG. 6, a docking port (21A) and an electrical port (21B) are provided on the bottom of the smart medicine container (10). It also houses the outlet door (22). FIG. 8 shows a 'sync cradle' (80) with a docking terminal (81) and an electrical terminal (82) that are adapted for operative engagement with the docking port (21A) and electrical port (21B) of the smart medicine container. Three communication ports (83) are also provided. The docking port (21A) along with the docking terminal (81) and communication ports (83) enable the smart medicine container (10), while it is sits in the sync cradle, to communicate with external communication devices. An electrical inlet (84) is provided which, along with electrical terminal (82) and electrical port (21B) powers the smart medicine container during the time it sits in the sync cradle (80). The sync cradle (80) is provided as an optional gadget that would help reduce the size and weight of the smart medicine container (10) and improve its portability. It also provides a more convenient way to transfer data between the smart medicine container (10) and other computing devices such as a pharmacy or physician computer. Now let us turn our attention to FIGS. 14A-C, where construction and operation of an alternate embodiment of the 'sync cradle'—the 'docking station' (140) for smart medicine container (10) is described. The docking station (140) is made of plastic of any other suitable material and comprises of receptacles of a size to accommodate the bottom of the smart medicine container (10). The docking station (140) can be made in multiple configurations; one unit, two units, four units, and six units etc. The basic design is the same for all, with differences in sizes and the internal USB hub board. The case consists of a contoured top and flat bottom. The top is shaped to accept the smart medicine container (10) unit. An off-centered protrusion insures the unit is placed into the docking station (140) correctly. Half round protrusions (142) on each side of the recessed area insure proper engagement with the smart medicine container (10) unit which will also insure proper contact with the USB unit (141) to docking station connections (21A & 21B in FIG. 6). There is an opening along one side for a standard USB port (145). The bottom plate of the docking station (140) has four feet. At the heart of the docking station (140) is a printed circuit board that is the USB board. This board is a USB hub that also converts the standard USB connector to a flat contact connector that people are used to seeing on phone charging stations.

Operation:

According to one aspect of the present invention, a smart medicine container (10) is connected to the pharmacy computer using the communication ports (41). Alternatively, it can be connected to the pharmacy computer by placing it in the docking station (14) that is connected to the pharmacy computer. The smart medicine container (10) can also communicate with the pharmacy computer wirelessly using the wireless transceiver. Pharmacist enters the medicine data into pharmacy computer including medicine name, strength, dose, frequency, physician information, authorized refills, expiration date and other relevant information. The pharmacist also enters the time the first dose is to be dispensed and time from which automatic dispensation will commence. The pharmacist can have pre programmed time regimen for various administration schedules. For example QID regimen (four times a day) may mean that the medicine is to be taken at 8 AM, 12 PM, 4 PM and 8 PM everyday or it may mean that the medicine is to be taken at 7 AM, 11 AM, 3 PM and 7 PM everyday. Pharmacies can have their own time regimen. There can be a universal time regimen or there can be a time regimen customized according to patient's preference and habits. Additional data, like patient's allergies, drug to drug and drug to food interactions, medicine adverse/side effect can be entered. This information is transferred into the smart medicine container and stored in the memory chip (72) and displayed on the electronic display unit (25) of the smart medicine container (10). In effect, the electronic display unit (25) replaces the paper label of conventional medicine containers. Additionally, space may be provided in the back of the smart medicine container to apply traditional paper labels that we are accustomed to seeing on the plastic medicine containers. However, it is to be appreciated that the electronic display unit (25) provides a more dynamic, comprehensive and interactive platform to access information about the contained medicine. A short vide/audio clip containing prescription instruction, medication information, and related disease information is also preferably loaded into the internal memory of the smart medicine container. This can be done either at pharmacy where the prescription is filled or from a central server via the internet. This information is played back to the patient at pre determined intervals or when a medication dose is due to be taken. This acts to reinforce patient education about their medication regiment, disease condition and the importance of compliance. The printed circuit board (71) uses the entered information to regulate the dispensation of medicine and to perform other functions of the smart medicine container (10). It also uses this information to analyze and report patient's compliance with a medicine regimen. Using this system, the pharmacist has no additional responsibility besides his/her normal customary responsibility to enter pertinent medicine information in the pharmacy computer system, which then automatically programs the smart medicine container (10) with the same information.

Figure 9:
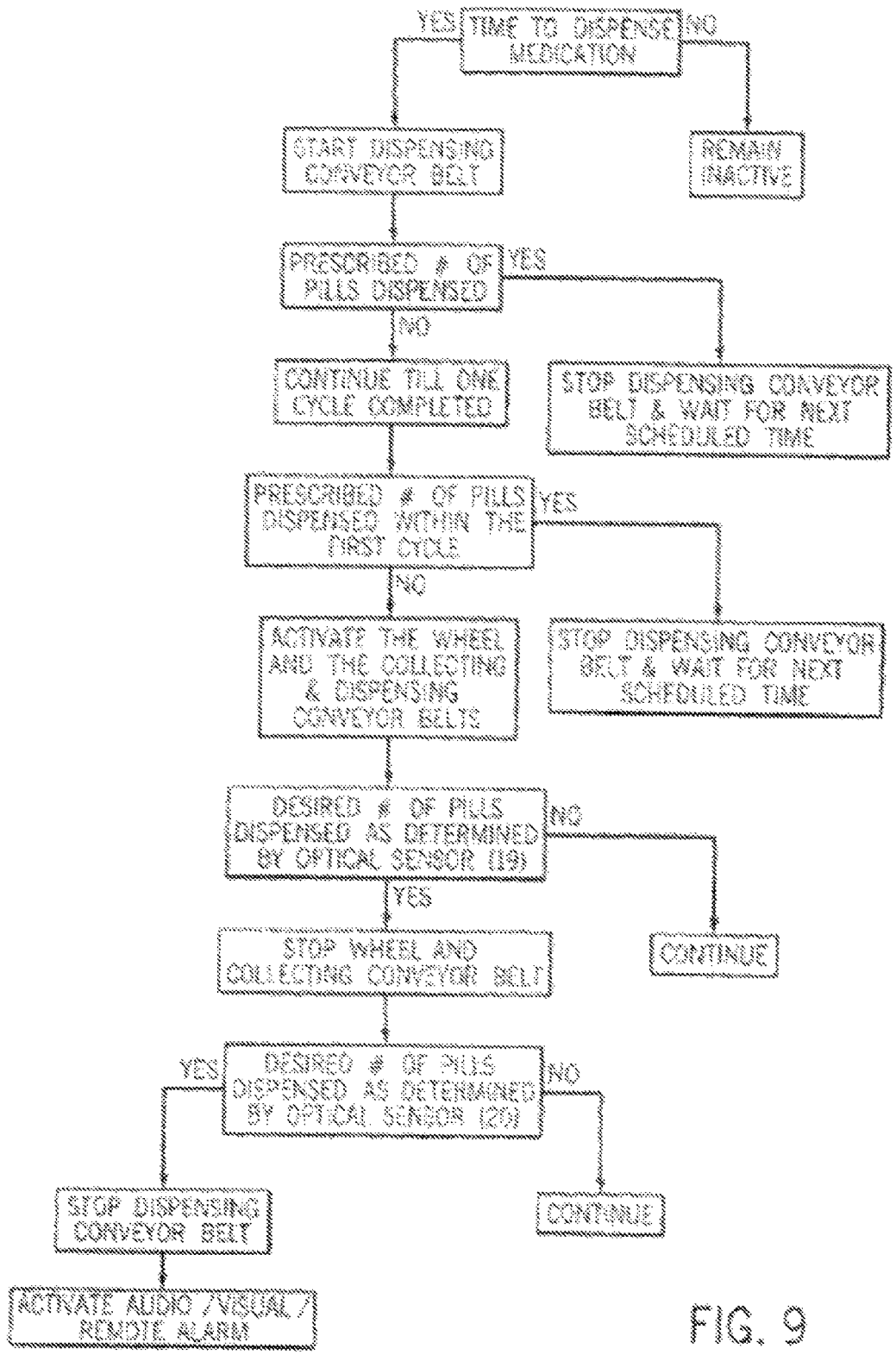
FIG. 9 shows an algorithm of the dispensation cycle of the smart medicine container.

FIG. 9 shows an algorithm that guides the pill dispensing assembly of the smart medicine container (10). Once the predetermined time to dispense medicine arrives, the regulating wheel is activated. The pill receptacles (24) of the regulating wheel (15) collect pills (121) from the storage compartment (11) and dispense them onto a moving collecting conveyor (16). The speed of the collecting conveyor (16) is greater than the rotational speed of the regulating wheel (15), which amplifies the pill separation provided by the regulating wheel (15). As the pills (121) fall off from the collecting conveyor (16) they are counted by photoelectric sensors (19), which relays the data to the printed circuit board (71). Once the printed circuit board (71) senses that desired number of pills (121) have been dispensed, it stops the regulating wheel (15). The collecting conveyor (16) transfers the pills (121) onto a moving dispensing conveyor (17). The dispensing conveyor (17) moves at a greater speed than the collecting conveyor which further amplifies the pill separation achieved so far. The dispensing conveyor (17) transfers the pills (121) into the dispensing compartment (13). The photoelectric sensors (20) count the pills (121) as they fall from the dispensing conveyor (17) into the dispensing compartment (13) and relay this data to the printed circuit board (71) and memory chip (72). The dispensing conveyor (17) stops once the printed circuit board (71) signals that prescribed quantity of pills (121) have been dispensed into the dispensing compartment (13). In effect, the entire pill dispensing assembly of the smart medicine container is inactivated at this time.

As shown in FIGS. 13A-E; once desired number of pills have been dispensed into the dispensing compartment at the end of a dispensation cycle; the recovery motor (303) moves the recovery cup (300) from resting position; as shown in FIG. 13A; to recovery position just below the outlet end of the dispensing conveyor (17); as shown in FIGS. 13B & 13C. There after, the collecting and dispensing conveyors move one complete cycle respectively to deposit pills remaining thereon into the recovery cup (300). The recovery motor (303) then moves the recovery cup (300) from recovery position; as shown in FIG. 13C upwards to resting position flush with the corresponding defect in the storage compartment (304); as shown in FIGS. 13D-E. During transit from the recovery position to resting position, the recovery cup (300) is inclined outwards from the counting compartment such that it prevents pills contained therein from falling into the counting compartment; as shown in FIGS. 13C-E. Once flush with the defect in the storage compartment (304) in resting position as in FIG. 13E, the recovery cup (300) is inclined inwards towards the storage compartment such that pills contained in the recovery cup (300) is deposited into the storage compartment by virtue of gravity. The pill recovery system and apparatus in essence recovers pills remaining on the collecting and dispensing conveyors after completion of a dispensation cycle and deposits the recovered pills back into the storage compartment for use in future dispensation cycles. This not only utilizes all pills in the smart medicine container for dispensation to the patient; but also keeps the collecting and dispensing conveyors free of pills between the dispensation cycles; improving the portability of the dispenser. For optimal functioning; the storage volume of the recovery cup (300) is greater than that of the volume of the pill receptacles (21) in the regulating wheel. Preferably the volume of the recovery cup (300) is greater than both the individual volume and the combined volume of the both pill receptacles (21). This feature guarantees that all the pills left over on the conveyor belts are able to be accommodated in the recovery cup (300) at the end of a dispensation cycle.

The time when a medicine dose is dispensed into the dispensing compartment (13) is recorded as the 'dispensation time' and serves as a measure of reliability of the smart medicine container (10). The reliability data is relayed to the printed circuit board (71) and memory chip (72) and can be viewed by an authorized user on the electronic display unit (25) or it can be downloaded to a computer and viewed. The reliability data is also relayed to and stored in a web server and can be accessed by authorized users. The smart medicine container (10) gives an audio and/visual alarm (26) to alert the patient that a medicine dose is dispensed and ready to be taken. In addition, after a reasonable wait time after the actual due time, the smart medicine container sends a remote reminder to patient or caregiver by phone, fax, pager, cellular phone, internet or any other communication device preferred by the patient using the communications platform provided therein. The patient can turn off the alarm using a control switch (28). The alarm feature of the smart medicine container can also be turned off for a period of time using a control switch (28). This is useful when patients may not want to be disturbed by the alarm such as when they are asleep.

Once a medicine dose is dispensed, the outlet door (22) is unlocked. Alternatively, as shown in FIG. 13A, instead of a door, a dispensing cup (22) coupled to a photoelectric sensor is provided. The patient can open the door/withdraw the dispensing cup and can take his/her medicine. The time of opening of the outlet door (22)/operation of the dispensing cup (22) is recorded as 'consumption time' by the sensor (23) and stored in the memory chip. This data is useful in determining patient compliance with a medicine regimen. This mechanism allows passive recording of compliance data as opposed to active recording wherein patients are required to manually operate a switch to indicate medicine consumption. The compliance data is saved in the memory chip (72) and can be viewed by an authorized user on the electronic display unit (25) or it can be relayed to a personal computer and viewed by authorized users. The compliance data is also relayed to and stored in a central server and can be accessed by authorized users.

Figure 10:
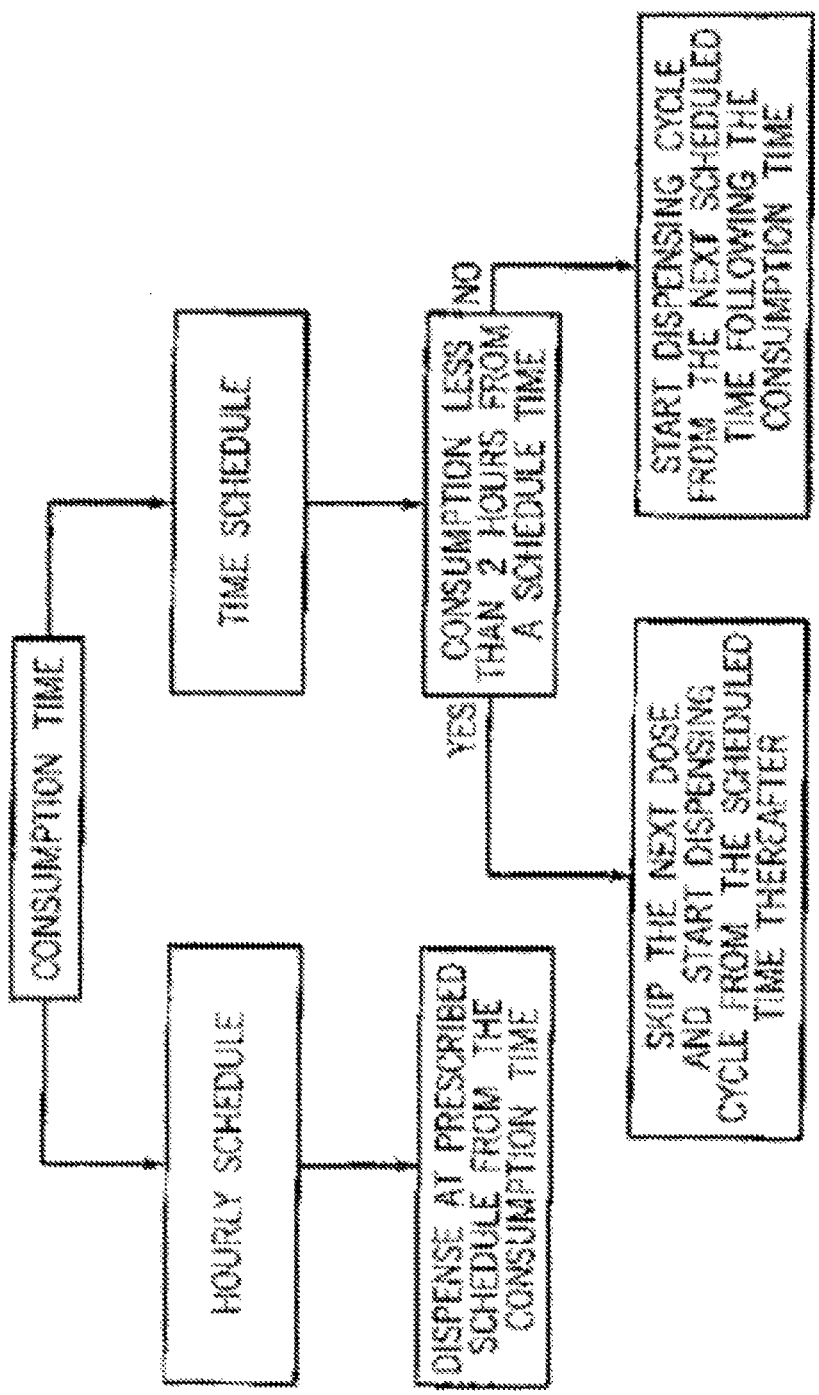
FIG. 10 shows an algorithm of the dispensation cycle of the smart medicine container in relation to the consumption time.

The electronic apparatus of the medicine container remains disabled until the outlet door (22) is opened and then closed. This ensures that another dose of medicine is not dispensed until the previous dose has been consumed. Consumption time is also used as a reference for timing the next dose. As shown in FIG. 10, for medicines that are to be taken at fixed hourly intervals, like every six hours, the next dose is dispensed at the prescribed interval from the consumption time. In case of medicines that are to be taken at certain times of the day, like four times a day, the next cycle starts according to a pre programmed algorithm. In the illustrated example of four times a day, if the consumption time is within 2 hours of a scheduled time, the dose due at that scheduled time is skipped and the dispensing cycle starts from the scheduled time thereafter. Otherwise, the dispensing cycle starts from the scheduled time following the consumption time. This is consistent with the current practice guidelines. Similarly, algorithms for other dosing schedules can be made according to accepted guidelines.

The smart medicine container (10) provides multiple unique safety features 1) the cap (14) of the storage compartment has a universal safety lock (73), which in the preferred embodiment is operable by a unique user identifier such as a unique password, RFID code, fingerprint scan, retinal scan etc. It allows only authorized access to the contents of the storage compartment of the smart medicine container (10). The universal safety lock (73) is operatively connected to the internal clock (preferably contained within the internal printed circuit board) and can be used for other useful purposes. Additionally the universal safety lock is operationally responsive to signal input from remote server. The universal safety lock (73) is programmed to remain open only during the time period when a medicine dose is prescribed to be taken. It is also programmed to automatically lock irreversibly once the contained medication is past its expiration date. The universal safety lock can also be programmed to lock irreversibly when there is a recall of medicine contained in corresponding smart medicine container unit. 2) The pill dispensing assembly of the smart medicine container automatically dispenses a prescribed quantity of medicine at desired times. In addition, the pill dispensing assembly remains inactive until the previously dispensed dose has been removed from the medicine container. These features allow access to only one prescribed dose of a medicine at any given time and that too, only when it is time to take a dose. This prevents overdose. In addition, the smart medicine container is programmed to disable the pill dispensing assembly if the contained medicine is past its expiration date. This feature prevents patients from consuming medicines that have expired. According to one method, medication expiration date is entered into the smart medicine container at the time a prescription is filled at the pharmacy. The Smart Medicine Container is then programmed to disable the internal circuitry at the time of medication expiration. According to another method, medication expiration date is entered into a central server in communication link with smart medicine container. The central server is programmed to communicate a 'kill signal' to the smart medicine container at the time of expiration of the medicine. The smart medicine container can also be programmed to irreversibly lock the universal lock and/or the outlet door lock upon expiration or recall of the medication contained therein, as discussed above. 3) The outlet door (22) has a lock that remains locked from the time it is closed until the time a medicine dose is dispensed. This prevents patients from consuming more than prescribed dose of a medicine. Preferably the outlet door lock is made operable by unique patient identifier such as a unique password, RFID, fingerprint scan, retinal scan etc. This prevents the medication dose from being taken by a wrong individual. The outlet door lock (22) is operatively connected to the internal clock (preferably contained within the internal printed circuit board) and can be used for other useful purposes. Additionally the outlet door lock is operationally responsive to signal input from remote server. The outlet door lock is programmed to remain open only during the time when a medicine dose is dispensed and ready to be taken at prescribed times. It can also be programmed to automatically lock irreversibly once the contained medication is past its expiration date. The universal safety lock can also be programmed to lock irreversibly when there is a recall of medicine contained in corresponding smart medicine container unit. In addition, the smart medicine container is programmed to lock the outlet door irreversibly if the medicine in the smart medicine container (10) is past its expiration date. This feature of the smart medicine container prevents patients from gaining access to an expired medicine. According to another embodiment of the present invention, the outlet door can have a lock that is coupled with a radiofrequency (RFID) reader. Access to the contents of the smart medicine container can be limited to authorized users with a corresponding RFID tag. According to yet another aspect, access to the storage compartment is restricted only to pharmacist/physician by means of the universal safety lock with a unique password known only to authorized users; and patient is allowed access only to the medicine in the dispensing compartment only at time when a medicine dose has been dispensed and due to be taken. This feature prevents misuse and diversion of medications such as opioid narcotics. Patient access to the outlet door is restricted at other times by means of a safety lock that remains in engaged position at all times except when a medicine dose has been dispensed and due to be taken. Many available locking mechanisms can be used for the universal safety lock and the outdoor lock (example latch type); and the type of locking mechanism should not be considered limiting. The locking mechanism is operatively connected to a 'user identifier' input means such as a touch screen monitor, finger print or retinal scanner, RFID transmitter and the like.

According to another aspect of the present invention, the locking apparatus containing a RFID reader can be used for other applications in the pharmaceutical industry. For example, medicine dispensing units used in hospitals can have a lock coupled with a RFID reader. This lock is operable when the RFID reader reads an authorized RFID tag. Authorized RFID tags are given only to authorized users. According to another aspect of the present invention, RFID reader can be coupled with any locking apparatus. The locking apparatus is made operable when the RFID reader of the locking apparatus reads an authorized RFID tag. It is to be appreciated that this feature of the present invention makes the operation of any such locking apparatus fast, secure and user friendly.

Figure 11:
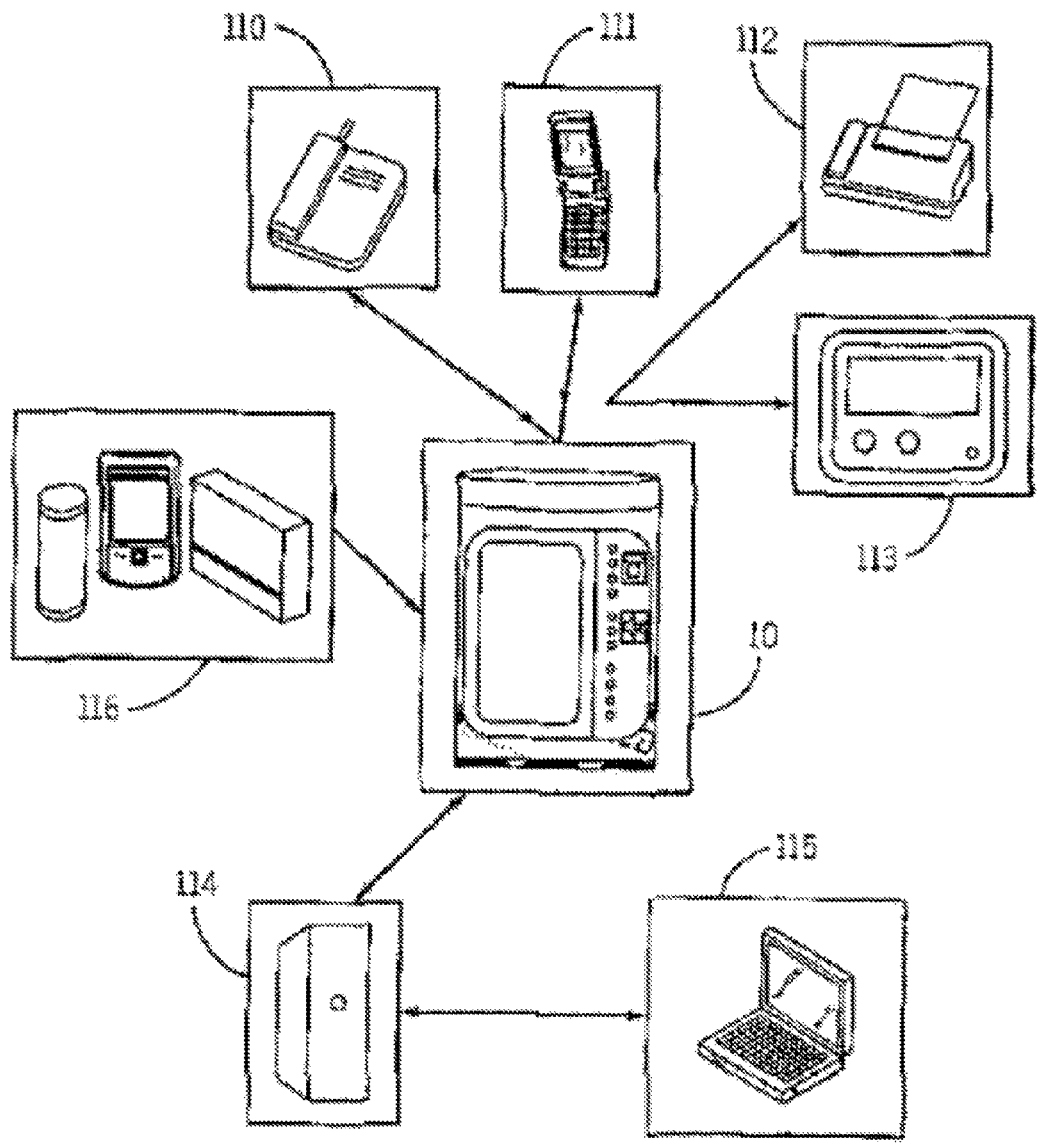
FIG. 11 shows the communication network of the smart medicine container.

According to another aspect of the present invention, a modem (51) and three communication ports (41) are provided in the smart medicine container (10). In the preferred embodiment, the modem (51) also has a two-way wireless transceiver. As shown in FIG. 11, the smart medicine container has means to communicate with external devices including communication devices such as personal computer; and medical devices; either by wired connection or by wireless connection. It can communicate with remote parties like physicians via external communication devices such as phone (110), pager (113), fax (112), cellular phone (111), computer (115), web server (114) and the like using phone line, wireless network, internet, LAN or any other communication network. The smart medicine container (10) is also able to communicate with appropriately configured medical devices such as glucose meter (116), blood pressure monitor, coagulation monitor and the like. Alternatively the smart medicine container is programmed to communication with a remote web server and a server application enables two-way communication between web server and external devices.

According to another aspect of the present invention, a multitude of smart medicine containers (10) are in communication link with a web server to form a network. The communication link between the web server and the smart medicine containers may be wireless or wired. Preferably the communication link comprises of smart medicine container unit in communication link with personal computer which in turn is in communication link with web server. Each smart medicine container (10) has a unique identifier that is readable by the web server. In the preferred embodiment, the unique identifier is a smart medicine container unit specific number stored in corresponding memory chip (72). The web server has access to data from all smart medicine containers in its network. The server synchronizes with the smart medication containers in its network at frequent intervals to keep the data updated. Synchronization is preferably actuated when the smart medicine container is resting in the docking station and connected to an internet enabled personal computer; or it can be done on a stand alone basis by each smart medicine container unit by direct wireless/wired communication link with the web server. This has many practical applications—1) The server compiles and stores patient compliance data and/or smart medicine container reliability data from the smart medicine containers within its network; 2) The web server stores the medicine inventory data for individual smart medicine containers within its network; 3) The web server serves as a nodal point for communication between the smart medicine container and remote parties like health care providers, enabling them to access patient compliance data and remotely control the functions of the smart medicine container; 4) The web server stores back up data for the smart medicine containers within its network; 5) The web server remotely uploads, edits and actuates the firmware loaded into the printed circuit board (71) and/or edit the information contained in the memory chip of the smart medicine containers (10) within its network and thereby, remotely controls the functions of the smart medicine container (10). These features have many practical applications some of which are discussed below.

1) Remote Medicine Management: The smart medicine container (10) sends remote reminders to patient or their caregiver when a medicine dose is ready to be taken. The smart medicine container (10) receives instructions remotely from health care professionals via communications network described above; and the printed circuit board of the corresponding smart medicine container accordingly initiates, modifies or discontinues a medicine regimen. It is to be appreciated that patient has no additional learning to do when these changes are made as the smart medicine container (10) automatically dispenses medicine according to the new dispensing instructions. The changes and the new instructions are displayed on the electronic display unit (25) or played in audio using the speakers (27). It is also to be appreciated that patient does not need to go to a health care professional or pharmacist for these changes to be made or to be educated about their new medicine regimen. Similarly, the smart medicine container (10) sends an automatic reminder to the pharmacist when refills are due. These features are of particular benefit to the elderly as they frequently have trouble learning new information and are commonly unable to drive.

2) Health Education: Health information is uploaded into the memory chip (72) at the time a prescription is filled or it can be uploaded remotely via the communications network described above. Patients view this information on the electronic display unit (25) or it can be played in audio using the speakers (27). The strategic timing of providing health information at the time of consumption of medicines provides a powerful learning tool and results in improved and lasting retention of the given information. It is also to be appreciated that the smart medicine container provides a dynamic, interactive and flexible platform for health education wherein different messages can be displayed at different times and in different formats.

3) Disease Management: The communications network enables the smart medicine container (10) to communicate with other appropriately configured peripheral medical devices such as blood pressure monitor, glucose meter, coagulation meter and the like. The printed circuit board is preferably pre programmed with instructions on changes to be made based on information received from medical devices; and is further programmed to initiate, change or discontinue a medicine regimen based on information received from the medical devices. The smart medicine container is preferably pre programmed at the time of filling a prescription at pharmacy or alternatively is programmed remotely via its communications network. According to another method, data obtained from peripheral medical devices is communicated to a health care professional who is them able to remotely change a medicine regimen using the communications network of the smart medicine container. It is evident from the foregoing discussion that the smart medicine container (10) can play an important role in comprehensive disease management and improve clinical outcomes. This unique feature of the present invention also reduces the need for a patient to go to physician's office and reduces or eliminates home visits by nurses for medication management.

4) Epidemic Control: A multitude of smart medicine containers (10) are in communication link with remote web server and form a network. The web server stores medicine regimen data saved in all smart medicine containers (10) within the network. In the event of an epidemic, the web server sends a command to all smart medicine containers (10) in its network containing effective medicine against the epidemic, instructing the pill dispensing assembly therein to dispense prescribed doses and alert the patient. In addition, the web server sends information about the epidemic to all smart medicine containers (10) within the network. This information is displayed on the electronic display unit (25) or played in audio using the speakers (27). It is to be appreciated from the foregoing discussion that the smart medicine container (10) can be a powerful tool in controlling an epidemic by 1) instantly dispensing effective medicines to a large number of at risk patients; and 2) quickly disseminating information about the epidemic, including preventive measures, to a large number of people.

5) Medicine Recall: Medicines are sometimes recalled from the market based on newly discovered adverse effects. A multitude of smart medicine containers (10) are in communication link with remote web server and form a network. The web server stores medicine regimen data saved in all smart medicine containers (10) within the network. In the event of a medicine recall, the web server instructs all smart medicine containers within the network containing the recalled medicament to immediately stop dispensing the said medicament. The web server also instructs the smart medicine containers in its network to display the recall information on their electronic display units. It is evident from the above discussion that the smart medicine container enables a quick, safe and extremely cost effective method to withdraw a medicine from the market.

6) Web Based Medicine Inventory Management System: This feature provides a dynamic inventory status of the smart medicine containers within a network and can be helpful in inventory management and product tracking. A multitude of smart medicine containers (10) are in communication link with remote web server and form a network. The web server stores medicine regimen data saved in all smart medicine containers (10) within the network. A pharmacy can review the inventory of all smart medication containers within its network and quickly assess the demand for various medicines based on the remaining refills. It can then accordingly stock its inventory and update its supply chain.

7) Web Based Compliance Monitoring System: A multitude of smart medicine containers (10) are in communication link with remote web server and form a network. The web server has access to and stores medicine compliance data saved in all smart medicine containers (10) within the network. Patient compliance data is communicated by smart medicine container to corresponding web server using the communication network described above. Patient compliance data stored in the web server is then made accessible to authorized users such as physicians, care givers and pharmacists. The web server stores compliance data from all smart medicine containers in its network. In addition, an interactive web site and intelligent application software capable of data analysis can provide a comprehensive solution in dose administration of non complaint patients. This data can also be helpful to researchers in studying, among other things, epidemiology of diseases and patient behavior patterns.

Pill bridging is a major problem with any pill dispensing assembly. The present invention has multiple unique features that prevent pill bridging. The first layer of protection is provided by the 'U' or 'V' shaped storage compartment (11) with a regulating wheel (15) with pill receptacles (24) guarding its outlet. This assembly enables an orderly and controlled discharge of pills (121) from the storage compartment onto the collecting conveyor (16). The use of gravitational force to discharge pills (121) from the pill receptacles of the regulating wheel onto the collecting conveyor (16) provides the second layer of protection against pill bridging. Even if multiple pills (121) are present in the receptacle, each is discharged at a different instance, thus providing pill separation. The collecting conveyor (16) moves at a faster speed than the rotational speed of the regulating wheel (15) which provides the third layer of protection against pill bridging. It amplifies the pill separation provided during discharge of pills (121) from the regulating wheel (15). The pills (121) are then discharged onto the dispensing conveyor (17). The separation of pills (121) at this stage is further amplified by moving the dispensing conveyor (17) at a faster speed than the collecting conveyor (16). This provides the fourth layer of protection against pill bridging. We believe that these four layers of protection provide a very reliable mechanism to prevent pill bridging and allow for an accurate dispensation of prescribed quantity of medicine.

Figure 12:
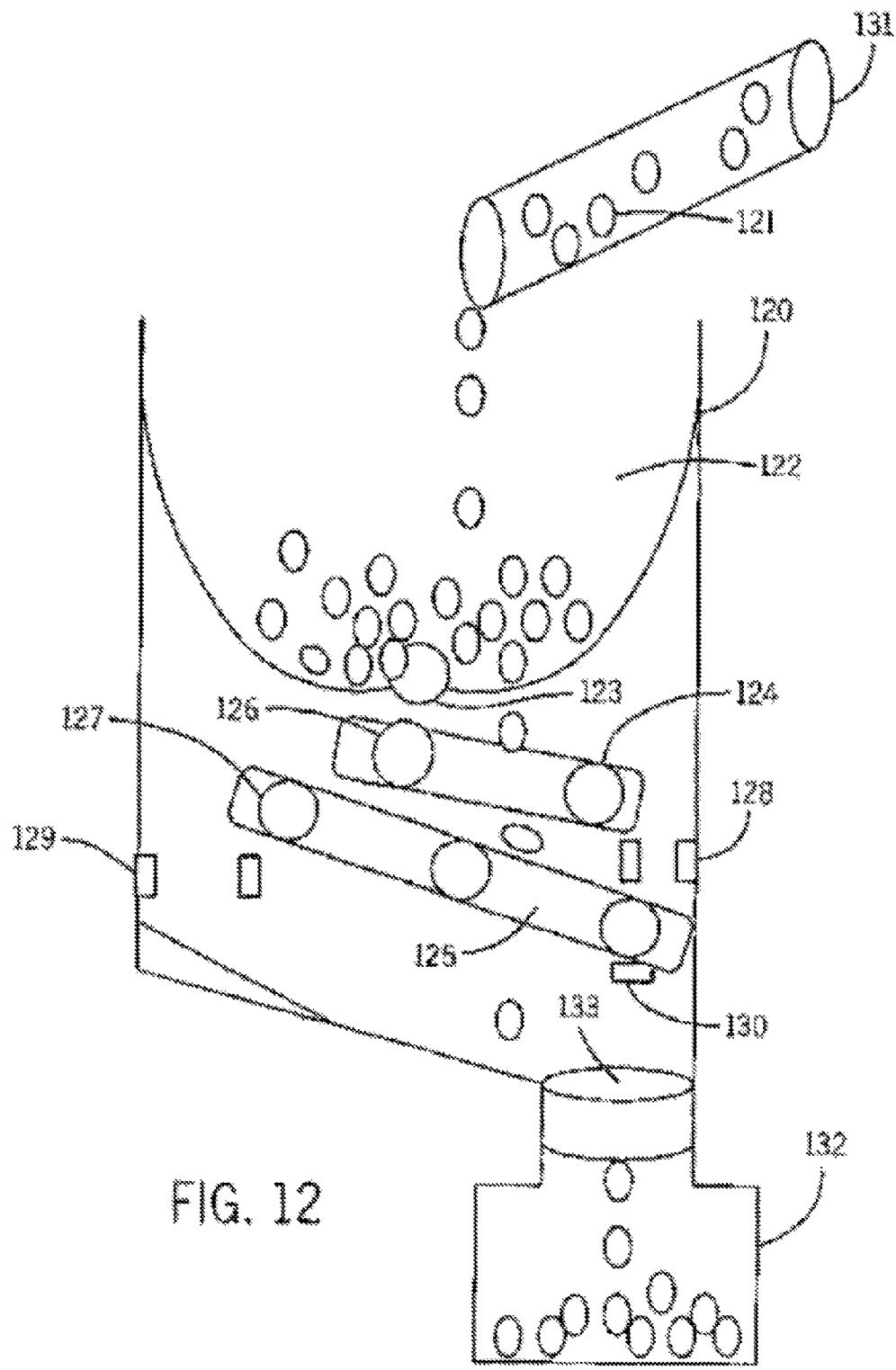
FIG. 12 shows the pill dispensing assembly of the present invention adapted for use in the pharmaceutical industry, such as to fill multiple pill bottles with a fixed quantity of pills.

According to another aspect of the present invention, the pill dispensing assembly can be adapted for use in the pharmaceutical industry to dispense a desired quantity of medicine, such as to fill a prescription at the pharmacy or to fill multiple medicine bottles with a fixed number of pills. This aspect of the present invention is shown in FIG. 12. The pill dispensing assembly is placed in housing (120) which has a storage tank (122) on top, dispensing assembly in the middle and an outlet bay at the bottom. Pills (121) are conveyed into the storage tank (122) using an appropriate mechanical assembly, which in the preferred embodiment is a tube (131). The outlet from the storage tank (122) into the dispensing assembly is guarded by a regulating wheel with two receptacles (123). The outlet door (133) at the bottom of the housing is coupled with a pill bottle (132). The dispensing assembly comprises of a collecting conveyor (124) and a dispensing conveyor (125) that move on two separate sets of wheels (126&127). Photoelectric sensors (128&129) are provided along the path of relay of pills between the collecting conveyor (124) and the dispensing conveyor (125) and between the dispensing conveyor (125) and the outlet bay. A photoelectric sensor (130) is also provided at the outlet door (133) which is activated when the pill bottle (132) is removed from the outlet door (133). A separate control unit housing a processor, memory chip and a plurality of control switches is provided (not shown). Once the command to dispense pills is given, the dispensing conveyor (125) is activated. This ensures that any remaining pill on the dispensing conveyor (125) from previous cycle is dispensed before a fresh batch is released from the storage tank (122). The dispensing conveyor (125) stops if desired number of pills (121) is dispensed before completion of one cycle. If the desired number of pills (121) is not dispensed within the first cycle, the remainder of the pill dispensing assembly comprising of the regulating wheel (123) and collecting conveyor (124) is activated. The pill receptacles of the regulating wheel (123) collect pills (121) from the storage tank (122) and dispense them onto a moving collecting conveyor (124). The speed of the collecting conveyor (124) is greater than the rotational speed of the regulating wheel (123) which amplifies the pill separation provided by the regulating wheel (123). As the pills (121) fall from the collecting conveyor (124) onto the dispensing conveyor (125), they are counted by photoelectric sensors (128), which relay this data to the processor and memory chip. Once the processor senses that desired number of pills (121) have been dispensed, it stops the regulating wheel (123) and the collecting conveyor (124). The collecting conveyor (124) transfers the pills (121) onto a moving dispensing conveyor (125). The dispensing conveyor (125) moves at a greater speed than the collecting conveyor (124) which further amplifies the pill separation achieved so far. The dispensing conveyor (125) transfers the pills (121) into the outlet bay. The photoelectric sensors (129) count the pills (121) as they fall from the dispensing conveyor (125) into the outlet bay and relay this data to the processor and memory chip in the control unit. The dispensing conveyor (125) stops once the processor signals that desired quantity of pills (121) have been dispensed. In effect, the entire pill dispensing assembly of the smart medicine container is inactivated at this time. Alternatively, in situations where a fixed number of pills is to be dispensed in multiple pill bottles, the filled pill bottle (132) is replaced by an empty pill bottle at the outlet door (133). The removal of the pill bottle (132) from the outlet door (133) is captured by a photoelectric sensor (130), which relays this information to the processor which keeps a count of the number of pill bottles that have been removed. The replacement of pill bottles at the outlet door (133) can be done manually or can be done automatically using a conveyor assembly. The pill recovery system and apparatus discussed in preceding paragraphs can also be applied to this alternate embodiment of the invention.

Figure 14A:
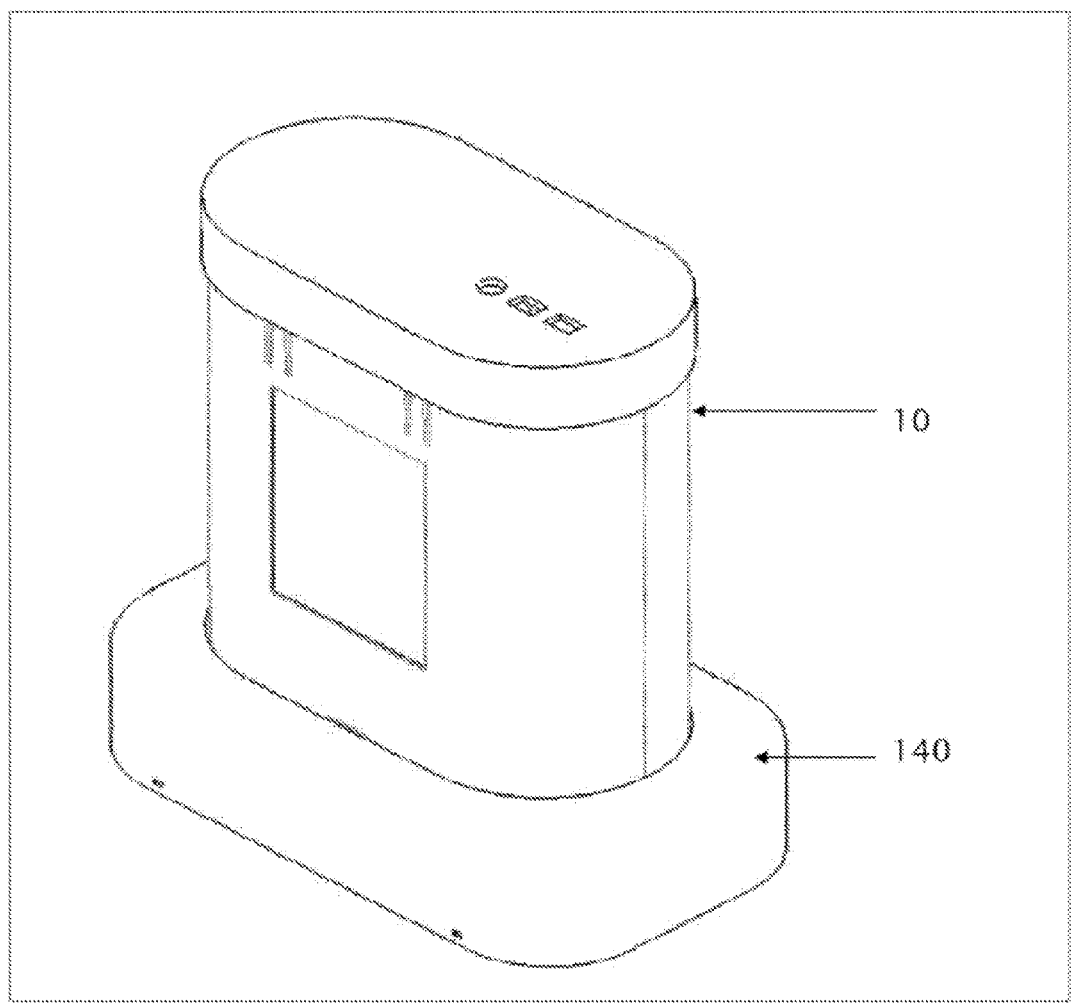
FIGS. 14A-C shows the construction and workings of docking station for smart medicine container.
Figure 14B:
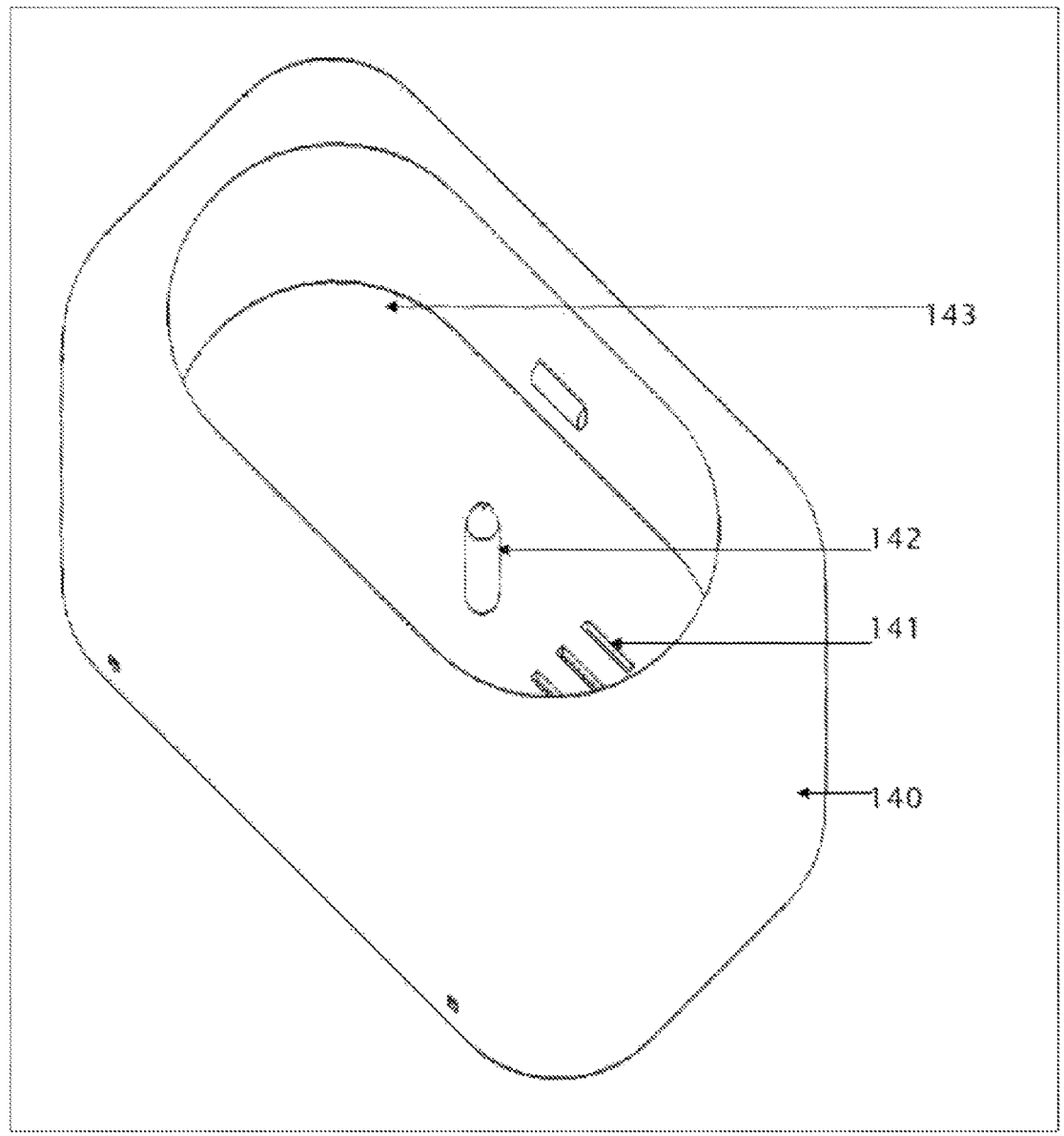
Figure 14C:
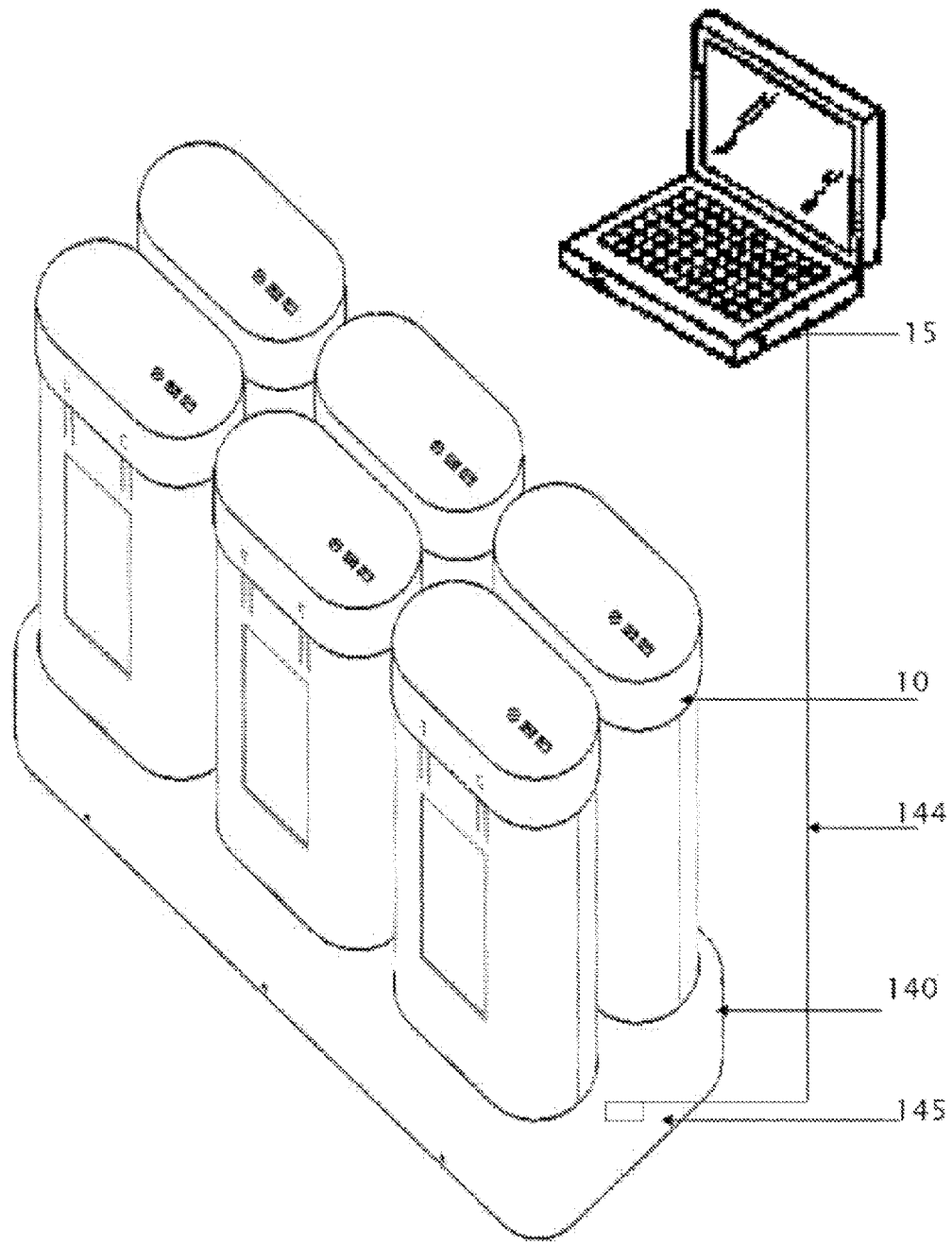

Now let us turn our attention to FIGS. 14A-C where construction and operation of the docking station (140) for smart medicine container (10) is described. The docking station (140) is made of plastic of any other suitable material and comprises of receptacles of a size to accommodate smart medicine container (10) unit. The docking station (140) can be made in multiple configurations; one unit, two units, four units, and six units etc. The basic design is the same for all, with differences in sizes and the internal USB hub board. The case consists of a contoured top and flat bottom. The top is shaped to accept the smart medicine container (10) unit. An off-centered protrusion insures the unit is placed into the docking station (140) correctly. Half round protrusions (142) on each side of the recessed area insure proper engagement with the smart medicine container (10) unit which will also insure proper contact with the USB unit (141) to docking station (140) connection. There is an opening along one side for a standard USB port (145). The bottom plate of the docking station (140) has four feet. At the heart of the docking station (140) is a printed circuit board that is the USB board. This board is a USB hub that also converts the standard USB connector to a flat contact connector that people are used to seeing on phone charging stations. The board will transfer signals to and from the personal computer as well as provide power to each smart medicine container (10) unit for operation and charging. If a PC is not being utilized, a USB to AC plug adapter can be used at the end of the USB cable instead. Operationally, when a smart medicine container (10) unit is positioned in the docking station (140), patient compliance data stored in the internal memory of the smart medicine container unit is transmitted to an application in the personal computer; wherefrom it is preferably transmitted for storage to a remote web server. Authorized users can access patient compliance data from the remote web server using an internet enabled communication device. Any updates to the firmware application in the smart medicine container are downloaded from remote web server/personal computer to the smart medicine container (10) using the docking station. In case of multi unit docking station (140); the clock in the smart medicine container (10) in each unit is synchronized, preferably with the clock in the personal computer/web server; to enable simultaneous dispensation of medicines from multiple smart medicine containers (10) with identical dispensation schedule. According to another aspect; means is provided for user to enter preferred dispensation times for various dispensation schedules (i.e. QDAY at 9 AM, BID at 9 AM and 6 PM, TID at 9 AM, 1 PM and 6 PM etc.) into the application in personal computer/web server. When smart medicine container (10) units are housed in the docking station are in communication link with personal computer/web server via the docking station (140); user selected dispensation times for different dispensation schedules are uploaded into the smart medicine container units (10). Thereafter; the medicines contained in the smart medicine container units (10) are dispensed according to prescribed dispensation schedule at corresponding preferred times selected by user. This feature along with synchronization of the smart medicine container (10) and personal computer/web server clocks ensures that medications contained in multiple smart medicine container units (10) with identical dispensation schedules are dispensed synchronously at preferred time corresponding to prescribed dispensation schedule as selected by the user.

What is claimed is:

1. A medicine container for securing accesses to a bulk supply of pills stored therein and one or more pills dispensed therein, the medicine container comprising:

a control unit having a processor, and programmed and configured to control operations of the medicine container;

a memory operatively coupled to the control unit and configured to store code and data used in connection with operations of the medicine container;

a communication interface unit operatively coupled to the control unit and configured to communicate with at least one of external and remote devices through at least one of communication interfaces and networks;

a pill-supply housing configured to store a bulk supply of pills;

a pill-supply locking means operatively controlled by the control unit, the pill-supply locking means configured to lock access to the pill-supply housing, and unlock access to the pill-supply housing only when an unlocking of access to the pill-supply housing is authorized by the control unit;

a dispensing assembly operatively controlled by the control unit, and configured to dispense one or more pills from among the stored bulk supply of pills based on dispensing schedule data stored in the memory;

a dispensed-pill housing configured to receive and store one or more pills dispensed by the dispensing assembly;

a dispensed-pill locking means operatively controlled by the control unit, the dispensed-pill locking means configured to lock access to the dispensed-pill housing, and unlock access to the dispensed-pill housing only when an unlocking of access to the dispensed-pill housing is authorized by the control unit; and wherein the control unit is programmed and configured to irreversibly cause the pill-supply locking means to lock access to the pill-supply housing and irreversibly cause the dispensed-pill locking means to lock access to the dispensed-pill housing, when the control unit receives discontinuing information indicating that the stored bulk supply of pills should permanently discontinue to be taken by a patient.

2. The medicine container of claim 1, wherein the discontinuing information is received from at least one of the memory and the communication interface unit.

3. The medicine container of claim 1, wherein the discontinuing information, as received by the control unit, comprises information indicating that the stored bulk supply of pills have already been expired.

4. The medicine container of claim 3, wherein the discontinuing information, as received by the control unit, comprises information indicating a current time and information indicating an expiration time of the stored bulk supply of pills.

5. The medicine container of claim 1, wherein the discontinuing information, as received by the control unit, comprises information indicating that the stored bulk supply of pills are subject to a medication recall.

6. The medicine container of claim 1, wherein the discontinuing information, as received by the control unit, comprises a kill signal instructing permanent disabling of the medicine container.

7. The medicine container of claim 1, wherein the control unit is further programmed and configured to disable the dispensing assembly from dispensing additional pills.

8. A method performed by a smart medicine container for securing accesses to a bulk supply of pills stored therein and one or more pills dispensed therein, the medicine container comprising: (a) a control unit having a processor and programmed and configured to control operations of the medicine container; (b) a memory operatively coupled to the control unit and configured to store code and data used in connection with operations of the medicine container; (c) a communication interface unit operatively coupled to the control unit and configured to communicate with at least one of external and remote devices through at least one of communication interfaces and networks; (d) a pill-supply housing configured to store a bulk supply of pills; e) a pill-supply locking means operatively controlled by the control unit, the pill-supply locking means configured to lock access to the pill-supply housing, and unlock access to the pill-supply housing only when an unlocking of access to the pill-supply housing is authorized by the control unit; (f) a dispensing assembly operatively controlled by the control unit, and configured to dispense one or more pills from among the stored bulk supply of pills based on dispensing schedule data stored in the memory; (g) a dispensed-pill housing configured to receive and store one or more pills dispensed by the dispensing assembly; and (h) a dispensed-pill locking means operatively controlled by the control unit, the dispensed-pill locking means configured to lock access to the dispensed-pill housing, and unlock access to the dispensed-pill housing only when an unlocking of access to the dispensed-pill housing is authorized by the control unit, the method comprising:

receiving, by the control unit, discontinuing information indicating that the stored bulk supply of pills should permanently discontinue to be taken by a patient;

verifying, by the control unit, from the received discontinuing information that the stored bulk supply of pills should permanently discontinue to be taken by a patient; and causing, by the control unit, the pill-supply locking means to lock access to the pill-supply housing irreversibly and causing, by the control unit, the dispensed-pill locking means to lock access to the dispensed-pill housing irreversibly.

9. The method of claim 8, wherein the discontinuing information is received by the control unit from at least one of the memory and the communication interface unit.

10. The method of claim 8, wherein the discontinuing information, as received by the control unit, comprises information indicating that the stored bulk supply of pills have already been expired.

11. The method of claim 10, wherein the discontinuing information, as received by the control unit, comprises information indicating a current time and information indicating an expiration time of the stored bulk supply of pills.

12. The method of claim 8, wherein the discontinuing information, as received by the control unit, comprises information indicating that the stored bulk supply of pills are subject to a medication recall.

13. The method of claim 8, wherein the discontinuing information, as received by the control unit, comprises a kill signal instructing permanent disabling of the medicine container.

14. The method of claim 8, further comprising disabling the dispensing assembly from dispensing additional pills.

* * * * *